United States Patent
Szymanski et al.

(10) Patent No.: US 9,221,898 B2
(45) Date of Patent: Dec. 29, 2015

(54) N-LINKED GLYCAN COMPOUNDS

(75) Inventors: Christine Szymanski, Edmonton (CA); Harald Nothaft, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 286 days.

(21) Appl. No.: 13/578,445

(22) PCT Filed: Feb. 11, 2011

(86) PCT No.: PCT/CA2011/050084
§ 371 (c)(1),
(2), (4) Date: Oct. 19, 2012

(87) PCT Pub. No.: WO2011/097733
PCT Pub. Date: Aug. 18, 2011

(65) Prior Publication Data
US 2013/0034556 A1 Feb. 7, 2013
US 2013/0295099 A2 Nov. 7, 2013
US 2014/0170150 A2 Jun. 19, 2014

Related U.S. Application Data

(60) Provisional application No. 61/303,411, filed on Feb. 11, 2010.

(51) Int. Cl.
*C07G 17/00* (2006.01)
*A61K 39/02* (2006.01)
*C07K 16/12* (2006.01)
*C07H 13/02* (2006.01)
*C08B 37/00* (2006.01)
*G01N 33/569* (2006.01)

(52) U.S. Cl.
CPC .............. *C07K 16/121* (2013.01); *A61K 39/105* (2013.01); *C07H 13/02* (2013.01); *C08B 37/00* (2013.01); *G01N 33/56922* (2013.01); *G01N 2333/205* (2013.01)

(58) Field of Classification Search
USPC ..................................... 536/123.1; 424/234.1
See application file for complete search history.

(56) References Cited

U.S. PATENT DOCUMENTS

| 2006/0165728 A1 | 7/2006 | Young et al. |
| 2010/0062484 A1 | 3/2010 | Aebi et al. |
| 2011/0039729 A1 | 2/2011 | Delisa et al. |
| 2013/0266604 A1 | 10/2013 | Szymanski et al. |

FOREIGN PATENT DOCUMENTS

| CA | 2607595 A1 | 11/2006 |
| CA | 2711307 A1 | 7/2009 |
| JP | S62500170 A | 1/1987 |
| WO | WO-86/01808 A1 | 3/1986 |
| WO | WO-2006/119987 A2 | 11/2006 |
| WO | WO-2009/104074 A2 | 8/2009 |
| WO | WO-2012/027850 A1 | 3/2012 |

OTHER PUBLICATIONS

Troutman et al., "Campylobacter jejuni PgIH is a single active site processive polymerase that utilizes product inhibition to limit sequential glycosyl transfer reactions," Biochemistry. 48(12):2807-2816 (2009).
International Search Report for International Application No. PCT/CA2011/050084, mailed Apr. 27, 2011 (5 pages).
Written Opinion of the International Searching Authority for International Application No. PCT/CA2011/050084, mailed Apr. 27, 2011 (5 pages).
International Preliminary Report on Patentability for International Application No. PCT/CA2011/050084, dated Aug. 14, 2012 (1 pages).
Extended European Search Report for European Patent Application No. 11741801.2, dated Sep. 3, 2013 (5 pages).
Alaimo et al., "Two distinct but interchangeable mechanisms for flipping of lipid-linked oligosaccharides," EMBO J. 25(5):967-76 (2006).
Aminian et al., "Expression and purification of a trivalent pertussis toxin-diphtheria toxin-tetanus toxin fusion protein in Escherichia coli," Protein Expr Purif. 51(2):170-8 (2007).
Bereswill et al., "Recent developments in Campylobacter pathogenesis," Curr Opin Infect Dis. 16(5):487-91 (2003).
Bullman et. al, "Campylobacter ureolyticus: an emerging gastrointestinal pathogen?" FEMS Immunol Med Microbiol. 61(2):228-30 (2011).
Butzler JP, "Campylobacter, from obscurity to celebrity," Clin Microbiol Infect. 10(10):868-76 (2004).
Chen MM et al., "From peptide to protein: comparative analysis of the substrate specificity of N-linked glycosylation in C. jejuni," Biochemistry. 46(18):5579-85 (2007).
Faridmoayer et al., "Extreme substrate promiscuity of the Neisseria oligosaccharyl transferase involved in protein O-glycosylation," J Biol Chem. 283(50):34596-604 (2008).
Feldman et al., "Engineering N-linked protein glycosylation with diverse O antigen lipopolysaccharide structures in Escherichia coli," Proc Natl Acad Sci U S A. 102(8):3016-21 (2005).
GenBank Accession No. CAL35542.1. submitted Aug. 14, 2006 (2 pages).
Gildersleeve et al., "Improved Procedure for Direct Coupling of Carbohydrates to Proteins via Reductive Amination," Bioconjug Chem. 19(7):1485-90 (2008).
Ihssen et al., "Production of glycoprotein vaccines in Escherichia coli," Microb Cell Fact. 9:61 (2010).
Kaida et al., "Antiganglioside antibodies and their pathophysiological effects on Guillain-Barré syndrome and related disorders—a review," Glycobiology. 19(7):676-92 (2009).

(Continued)

*Primary Examiner* — Jennifer Graser
(74) *Attorney, Agent, or Firm* — Clark & Elbing LLP

(57) ABSTRACT

An isolated or purified compound is provided, comprising A-GlcNAc[GlcNAc]-GalNAc-GalNAc-QuiNAc4NAc, wherein A is GlcNAc or Glc. There is further provided a vaccine based on such compound, having particular use to treat or prevent an infection caused by a *Campylobacter* organism. There is also provided an antibody or antisera against the compound, having particular use to diagnose the presence of an infection caused by a *Campylobacter* organism.

7 Claims, 24 Drawing Sheets

(56) References Cited

OTHER PUBLICATIONS

Kelly et al., "Biosynthesis of the N-linked glycan in Campylobacter jejuni and addition onto protein through block transfer," J Bacteriol. 188(7):2427-34 (2006).

Kowarik et al., "Definition of the bacterial N-glycosylation site consensus sequence," EMBO J. 25(9):1957-66 (2006).

Kowarik et al., "N-linked glycosylation of folded proteins by the bacterial oligosaccharyltransferase," Science. 314(5802):1148-50 (2006).

Liu et al., "Mass spectrometry-based glycomics strategy for exploring N-linked glycosylation in eukaryotes and bacteria," Anal Chem. 78(17):6081-7 (2006).

Makhlof et al., "Design and evaluation of novel pH-sensitive chitosan nanoparticles for oral insulin delivery," Eur J Pharm Sci. 42(5):445-51 (2011).

Manoharan et al., "UV resonance Raman spectra of bacteria, bacterial spores, protoplasts and calcium dipicolinate," J Microbiol Meth. 11(1):1-15 (1990).

NCBI Blast for UniProt Accession No. XP-002715424. Retrieved on Sep. 19, 2006 (1 page).

Nothaft et al., "N-linked protein glycosylation in a bacterial system," Methods Mol Biol. 600:227-43 (2010).

Nothaft et al., "Protein glycosylation in bacteria: sweeter than ever," Nat Rev Microbiol. 8(11):765- 78 (2010).

Nothaft et al., "Study of free oligosaccharides derived from the bacterial N-glycosylation pathway," Proc Natl Acad Sci U S A. 106(35):15019-24 (2009). (18 pages).

Parkhill et al., "The genome sequence of the food-borne pathogen Campylobacter jejuni reveals hypervariable sequences," Nature. 403(6770):665-8 (2000).

Reid et al., "Affinity-capture tandem mass spectrometric characterization of polyprenyl-linked oligosaccharides: tool to study protein N-glycosylation pathways," Anal Chem. 80(14):5468-75 (2008).

Reid et al., "Analysis of bacterial lipid-linked oligosaccharide intermediates using porous graphitic carbon liquid chromatography-electrospray ionization mass spectrometry: heterogeneity in the polyisoprenyl carrier revealed," Anal Chem. 81(20):8472-8 (2009).

Schwarz et al., "A combined method for producing homogeneous glycoproteins with eukaryotic N-glycosylation," Nat Chem Biol. 6(4):264-6 (2010).

Schwarz et al., "Relaxed acceptor site specificity of bacterial oligosaccharyltransferase in vivo," Glycobiology. 21(1):45-54 (2011).

Scott et al., "Simultaneous glycan-peptide characterization using hydrophilic interaction chromatography and parallel fragmentation by CID, higher energy collisional dissociation, and electron transfer dissociation MS applied to the N-linked glycoproteome of Campylobacter jejuni," Mol Cell Proteomics. 10(2):M000031-MCP201 (2011).

Symmons et al., "The assembled structure of a complete tripartite bacterial multidrug efflux pump," Proc Natl Acad Sci U S A. 106(17):7173-8 (2009).

Szymanski et al., "Campylobacter—a tale of two protein glycosylation systems," Trends Microbiol. 11(5):233-8 (2003).

Szymanski et al., "Detection of conserved N-linked glycans and phase-variable lipooligosaccharides and capsules from campylobacter cells by mass spectrometry and high resolution magic angle spinning NMR spectroscopy," J Biol Chem. 278(27):24509-20 (2003).

Szymanski et al., "Evidence for a system of general protein glycosylation in Campylobacter jejuni," Mol Microbiol. 32(5):1022-30 (1999).

Szymanski et al., "Protein glycosylation in bacterial mucosal pathogens," Nat Rev Microbiol. 3(3):225-37 (2005).

van Sorge et al., "N-glycosylated proteins and distinct lipooligosaccharide glycoforms of Campylobacter jejuni target the human C-type lectin receptor MGL," Cell Microbiol. 11(12):1768-81 (2009).

Wacker et al., "N-linked glycosylation in Campylobacter jejuni and its functional transfer into E. coli," Science. 298(5599):1790-3 (2002).

Wang et al., "A versatile bifunctional dendritic cell targeting vaccine vector," Mol Pharm. 6(1):158-72 (2009).

Yan et al., "Unraveling the mechanism of protein N-glycosylation," J Biol Chem. 280(5):3121-4 (2005).

Young et al., "Structure of the N-linked glycan present on multiple glycoproteins in the Gram-negative bacterium, Campylobacter jejuni," J Biol Chem. 277(45):42530-9 (2002).

Zhang et al., "Detection and isolation of Campylobacter species other than C. jejuni from children with Crohn's disease," J Clin Microbiol. 47(2):453-5 (2009).

Communication pursuant to Rules 70(2) and 70a(2) EPC for European Patent Application No. 11820973.3, dated Nov. 29, 2013 (1 page).

International Preliminary Report on Patentability and Written Opinion of the International Searching Authority for International Application No. PCT/CA2011/050535, mailed Mar. 14, 2013 (9 pages).

Patent Examination Report No. 1 for Australian Patent Application No. 2011298697, dated Apr. 16, 2014 (3 pages).

Supplementary European Search Report and Communication for European Patent Application No. 11820973.3, dated Nov. 12, 2013 (8 pages).

Office Action with English translation for Japanese Patent Application No. 2012-552217, mailed Apr. 21, 2015 (12 pages).

Office Action for U.S. Appl. No. 13/819,645, dated May 22, 2015 (20 pages).

Communication pursuant to Article 94(3) EPC for European Patent Application No. 11820973.3, dated Mar. 27, 2015 (5 pages).

English translation of Office Action for Japanese Patent Application No. 2013-526288, dated Jun. 18, 2015 (9 pages).

Examination Report for Australian Patent Application No. 2011214871, dated Sep. 23, 2015 (2 pages).

Figure3 D(1)
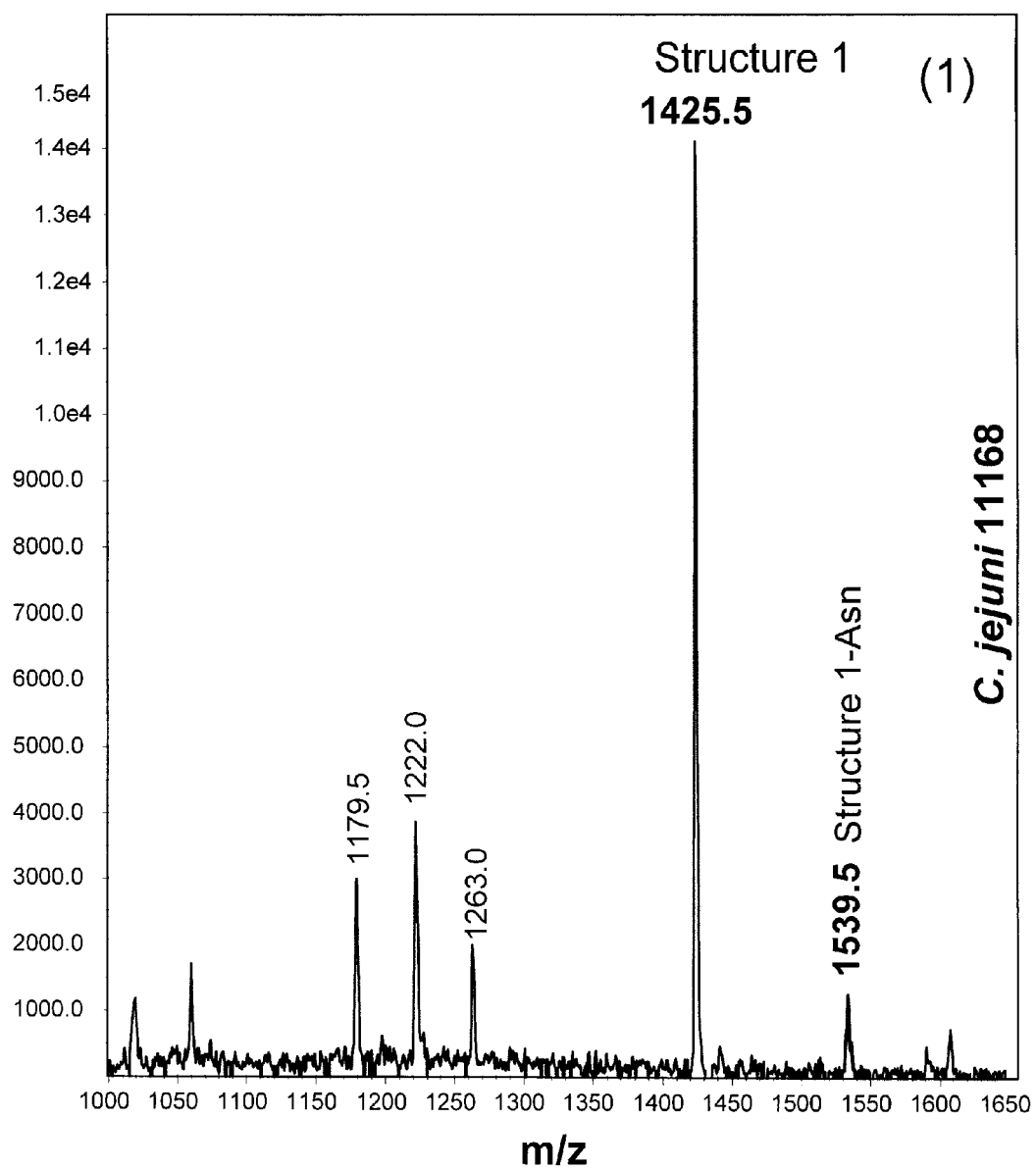

Figure3 D(2)
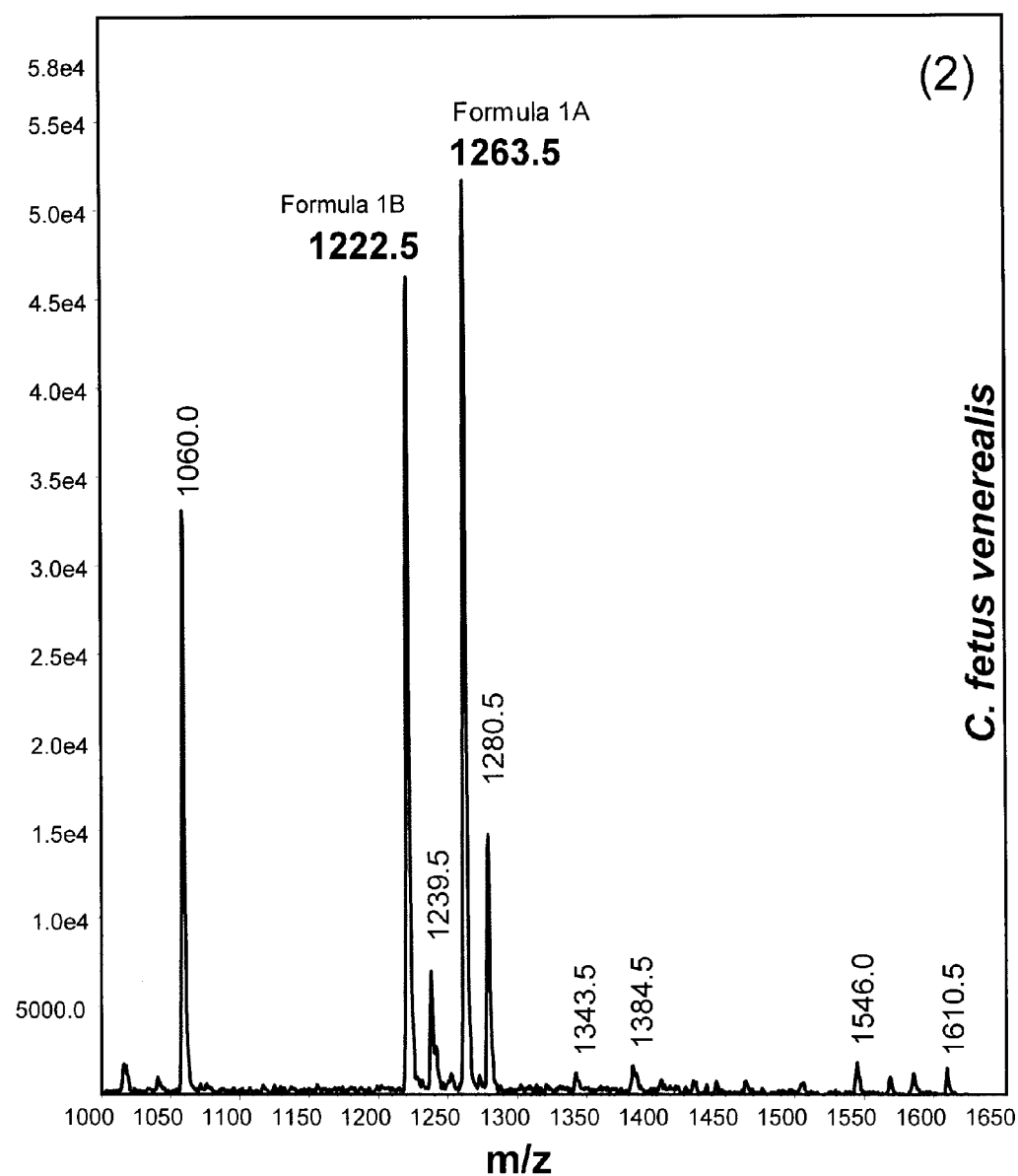

Figure3 D(3)
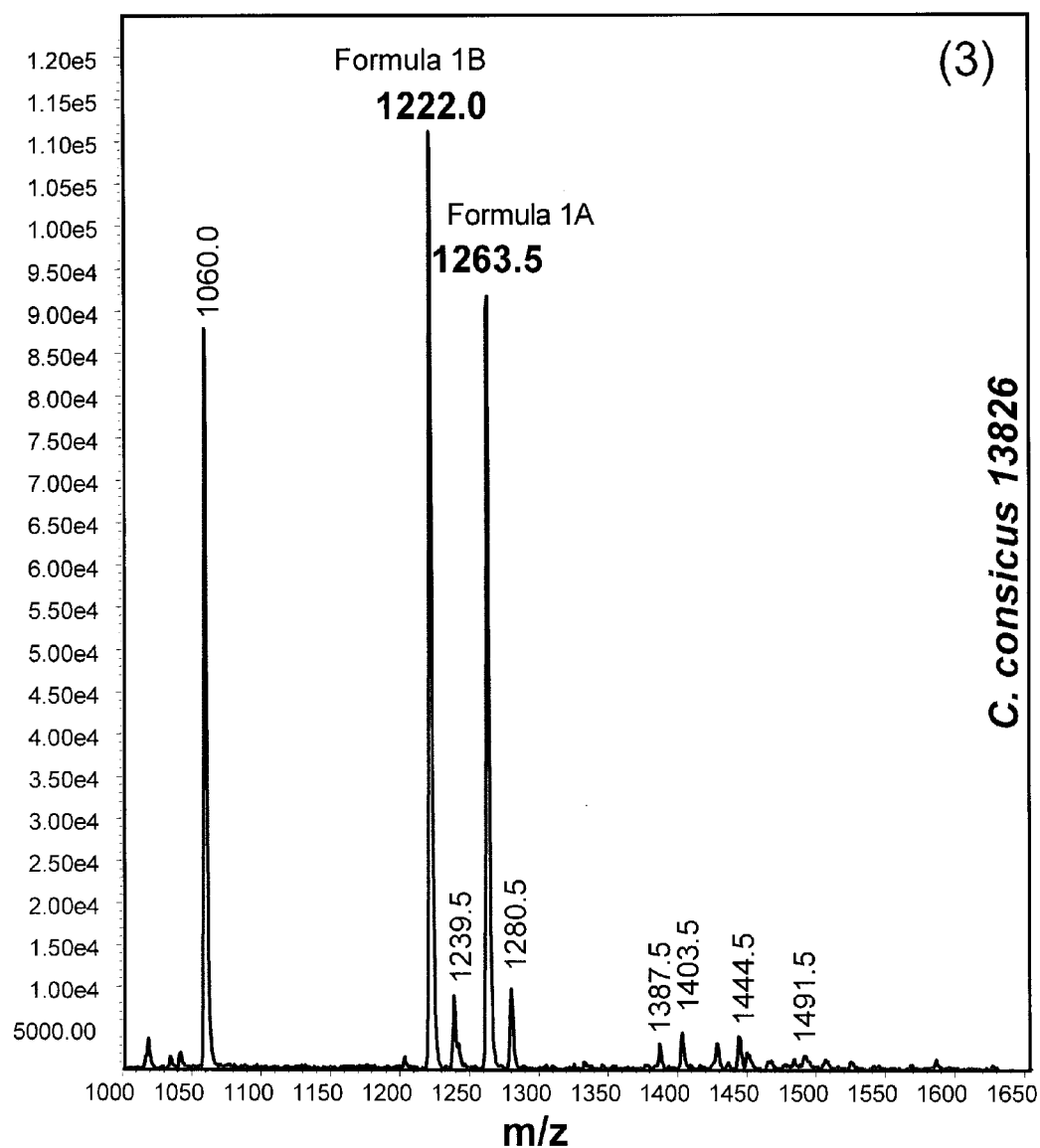

Figure3 D(4)
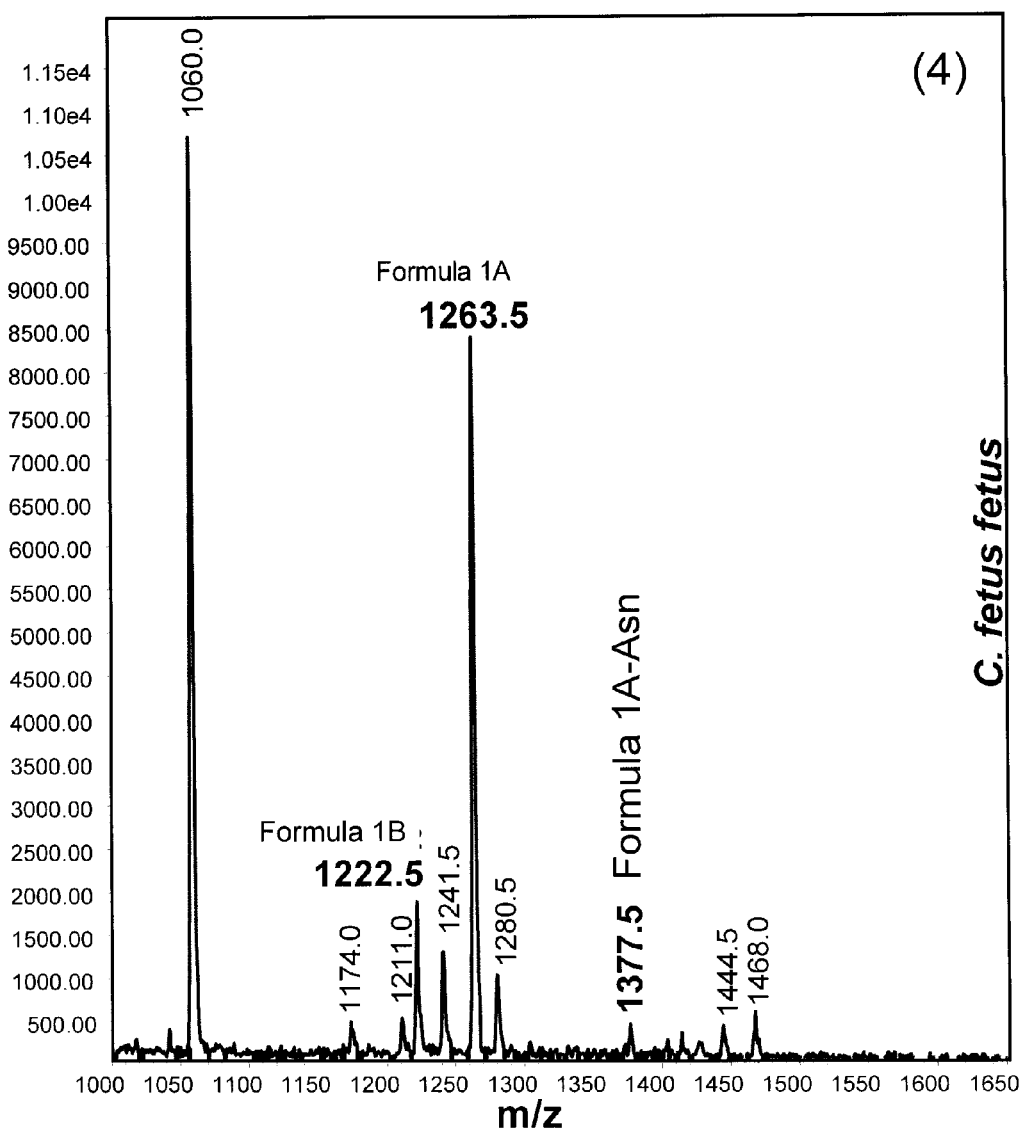

Figure3 D(5)
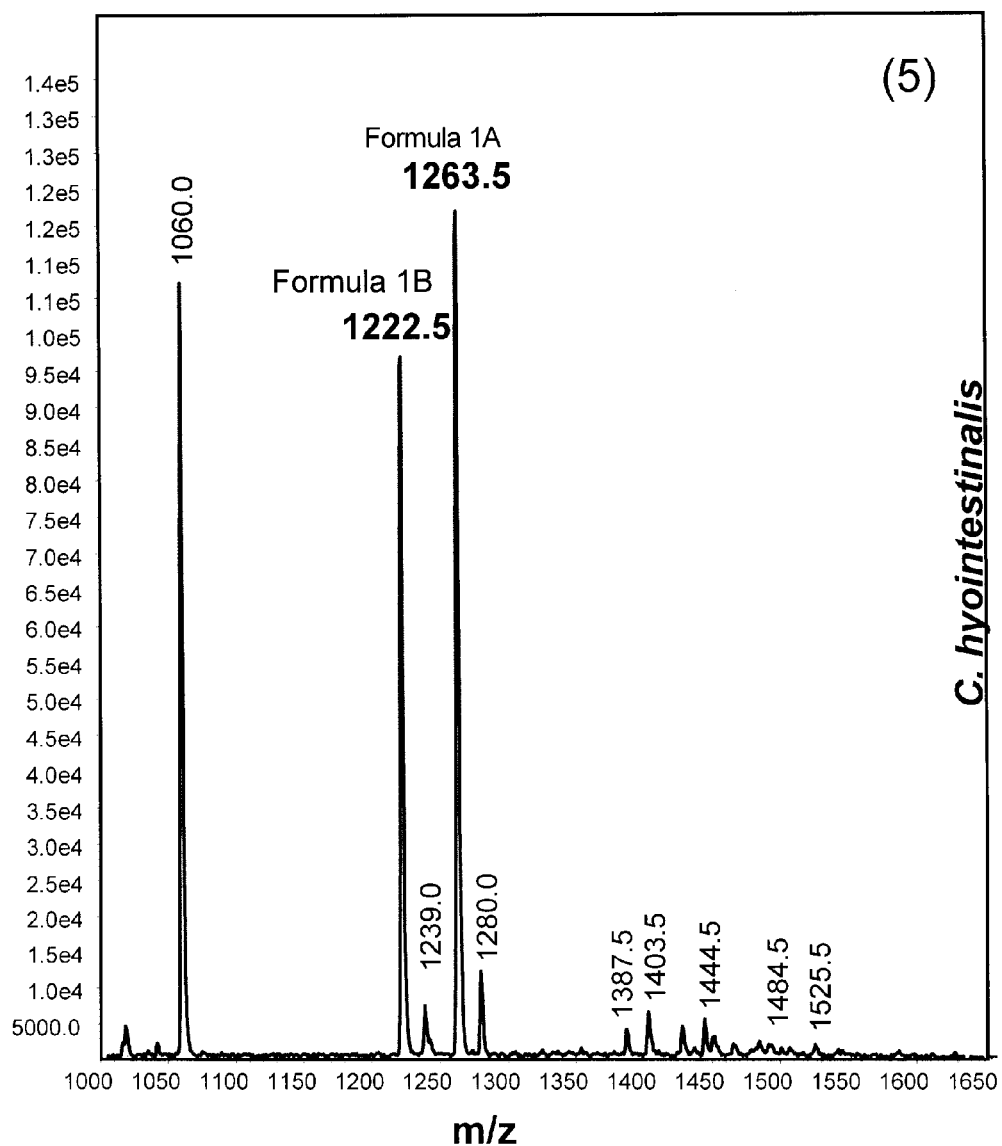

Structure 1

Formula 1A

Formula 1B

N-LINKED GLYCAN COMPOUNDS

CROSS REFERENCE TO RELATED APPLICATIONS

This application is the U.S. National Stage filing under 35 U.S.C. §371 of International Application No. PCT/CA2011/050084, filed on Feb. 11, 2011, which claims benefit of U.S. Provisional Application No. 61/303,411, filed on Feb. 11, 2010, each of which is hereby incorporated by reference in its entirety.

FIELD OF THE INVENTION

The invention relates to an N-linked glycan compound of Formula 1, which optionally may be fused or attached to an amino acid, peptide, protein or lipid. The invention further relates to antibodies and antisera against such compound, and the use thereof to diagnose an infection caused by a *Campylobacter* pathogen. The invention further relates to the use of the compound as a vaccine to treat or prevent infection by a *Campylobacter* pathogen.

BACKGROUND

*Campylobacter jejuni* and *Campylobacter* coil are the two most commonly isolated species of *campylobacter* that cause human infection. These organisms cause high rates of gastroenteritis worldwide, with the number of cases often exceeding that for *Salmonella, Shigella* and Enterotoxigenic *E. coli* combined (Butzler J P, Clinical Microbiology and Infection 2004). Furthermore, *C. jejuni* infection has been linked to the development of Guillain-Barré Syndrome, the most common cause of pathogen-caused paralysis since the eradication of polio (for reviews see: Kaida K, Glycobiology, 2009; Bereswill S & Kist M, Current Opinion in Infectious Diseases, 2003). Other *Campylobacter* species have been recognized as emerging pathogens in human gastroenteritis (*C. upsaliensis, C. hyointestinalis*) were associated with inflammatory bowel disease in children and with gingivitis, periodontitis, and human abortions (*C. retus, C. concisus*) (Zhang L S et al., Journal of Clinical Microbiology, 2009) and in causing venereal disease and infertility in livestock (especially cattle; *C. fetus venerealis*), and sheep abortions (*C. fetus fetus*) (Butzler J P, Clinical Microbiology and Infection, 2004 and references therein).

Since the publication of the first *C. jejuni* genome sequence in 2000 (Parkhill J et al., Nature, 2000), several other *campylobacter* genome sequences have been reported. Unlike the majority of bacteria that have been described to date, all campylobacters contain conserved pgl genes required for N-linked protein glycosylation (Szymanski C M & Wren B W, Nature Reviews Microbiology 2005; Nothaft H & Szymanski C M, Nature Reviews Microbiology, 2010).

In eukaryotes, glycosylated proteins are ubiquitous components of extracellular matrices and cellular surfaces. Their oligosaccharide moieties are implicated in a wide range of cell-cell and cell-matrix recognition events that are vital in biological processes ranging from immune recognition to cancer development. Glycosylation was previously considered to be restricted to eukaryotes, however through advances in analytical methods and genome sequencing, there have been increasing reports of both 0-linked and N-linked protein glycosylation pathways in bacteria (Nothaft H & Szymanski C M, Nature Reviews Microbiology, 2010). Since the discovery of the first general protein glycosylation pathway in bacteria (Szymanski C M et al., Molecular Microbiology 1999), the demonstration that the *C. jejuni* glycans are attached through an N-linkage en bloc (Kelly J H et al., Journal of Bacteriology 2006, Wacker M et al., Science 2002, Young N M et al., Journal of Biological Chemistry, 2002) and that the pathway not only can be functionally transferred into *Escherichia coli* (Wacker M et al., Science, 2002), but that the oligosaccharyltransferase enzyme (PglB) is capable of adding foreign sugars to protein (Feldman M et al., PNAS 2005), a surge of research activities has resulted in further characterization and exploitation of this system.

The detailed structure of the unique *C. jejuni* N-linked heptasaccharide has been described (Young N M et al., Journal of Biological Chemistry, 2002). Using methods such as high resolution magic angle spinning (HR-MAS) NMR (Szymanski C M et al., Journal of Biological Chemistry, 2003), it has been shown that this heptasaccharide is conserved in structure in both *C. jejuni* and *C. coli*.

An intermediate in the *C. jejuni* N-linked glycosylation pathway has been described, namely a free (oligo-) heptasaccharide (fOS)—a soluble component of the *C. jejuni* periplasmic space (Liu X et al., Analytical Chemistry, 2006). This fOS has the identical structure as the N-linked oligosaccharide added onto proteins (Nothaft H et al., PNAS 2009). Under laboratory growth conditions, the ratio of fOS versus heptasaccharide N-linked to protein is approximately 9:1. The fOS in *C. jejuni* plays a role in osmoregulation similar to bacterial periplasmic glucans and this pathway can be manipulated by altering the environmental osmolyte concentration (Nothaft H et al., PNAS 2009).

FIG. 1 shows N-linked protein glycosylation and free oligosaccharides in *C. jejuni*. The undecaprenyl-pyrophosphate-linked heptasaccharide is assembled in the cytosol by the addition of nucleotide activated sugars (Szymanski C M et al., Journal of Biological Chemistry, 2003; Szymanski C M et al., Trends Microbiology 2003). The complete heptasaccharide is translocated across the inner membrane to the periplasm by the ABC transporter PglK (Alaimo C et al., EMBO Journal, 2006). The oligosaccharide is transferred to the amino group of asparagine in the protein consensus sequence, D/E-X1-N-X2-S/T, wherein X1, X2 can be any amino acid except proline, by PglB (Kowarik M et al., EMBO Journal 2006; Young N M et al., Journal of Biological Chemistry, 2002). In addition, large amounts of free heptasaccharide (fOS) can be found in *C. jejuni* (Liu X et al., Analytical Chemistry, 2006); the fOS to N-glycan ratio was determined to be 9:1. GlcNAc, N-acetylgalactosamine; Bacillosamine (Bac), 2,4-diacetamido-2,4,6-trideoxyglucose; GalNAc, N-acetylgalactosamine; Glc, Glucose (adapted from Szymanski C M et al., Trends Microbiology, 2003).

SUMMARY

We have determined the N-glycan and fOS structures from a number of *Campylobacter* species, all of which possess N-linked glycans and fOS. In addition, we demonstrated that *campylobacter* N-glycans and fOS can be divided into two structural groups. The first group produces a similar structure to that published for *C. jejuni* and *C. coli* (Young N M et al., Journal of Biological Chemistry, 2002; Szymanski C M et al., Journal of Biological Chemistry, 2003). The second group produces a unique glycan structure which differs from that determined for *C. jejuni* and *C. coli* and that have never been described before. *Campylobacter* species that fall into this group include *Campylobacter fetus venerealis* (cause of venereal disease and infertility in cattle), *Campylobacter fetus fetus* (cause of sheep abortions), *Campylobacter concisus* (associated with gingivitis and periodontitis, and has been isolated from the feces of patients with gastroenteritis), *Campylobacter hyointestinalis* (like *C. jejuni* and *C. coli*, is associated with diarrheal disease) and *Campylobacter hyointestinalis* subspecies.

*Campylobacter sputorum* and *Campylobacter sputorum* subspecies, *Campylobacter lanienae*, *Campylobacter ureolyticus* (an emerging enteric pathogen suggested to be involved in gastroenteritis, Bullman S et al., FEMS Immunology & Medical Microbiology, 2010). *Campylobacter hominis, Campylobacter gracilis, Campylobacter rectus* (periodontal disease and human abortion), *Campylobacter showae, Campylobacter mucosalis* and *Campylobacter curvus* are believed to be within the second group.

FIG. 2 illustrates a phylogenetic analysis of the protein sequences of the key component of this pathway, the oligosaccharyltransferase (PglB) including the genome sequenced *Campylobacter* species and other related organisms and demonstrates that the Campylobacters divide into two groups. Within the *campylobacter* branch Structure 1 producing species are in the upper box, Formula 1A and Formula 1B producing strains are in the lower box (adapted from Nothaft H & Szymanski C M, Nature Reviews Microbiology, 2010).

FIG. 3: illustrates N-glycan reactivity towards (A) a *C. jejuni* N-glycan-specific antiserum, (B) SBA-lectin (recognizing terminal GalNAc residues of structure1) (C) WGA-lectin reactivity (recognizing terminal GlcNAc residues of Formula 1A and 1B with cross-reactivity to GalNAc structures) and (D) mass-spectrometry-based fOS analyses showed that pgl pathway derived glycans differ among *Campylobacter* species.

According to one aspect, the invention relates to a novel N-linked glycan (referred to as N-glycan) compound of Formula 1: A-GlcNAc[GlcNAc]-GalNAc-GalNAc-QuiNAc4NAc, wherein A is GlcNAc or Glc. This compound in its native form is common to several *Campylobacter* species. In its native form, the compound is soluble in the periplasm as well as attached to inner membrane and periplasmic proteins and most notably surface outer membrane proteins of many *Campylobacter* species, including pathogens.

In the present invention, the compound of Formula 1 is provided in isolated and/or purified form. The compound comprises two hexasaccharides which differ from each other in a terminal sugar, which comprises either Glc or GlcNAc. The first of said compounds is: GlcNAc-GlcNAc[GlcNAc]-GalNAc-GalNAc-QuiNAc4NAc (herein Formula 1A). The second of said compounds is: Glc-GlcNAc[GlcNAc]-GalNAc-GalNAc-QuiNAc4NAc (herein Formula 1B).

In the above Formula 1, QuiNAc4NAc represents an alternative signifier of the saccharide Bac, which constitutes an abbreviation of bacillosamine.

In one aspect the invention relates to an isolated or purified compound comprising the compounds of Formula 1 connected or linked to a single amino acid, an oligopeptide, a peptide, a protein, or a lipid. In one aspect, the oligopeptide or peptide comprises between 2 and 40 amino acids, or between 2 and 30 amino acids, or between 2 and 20 amino acids, or between 2 and 10 amino acids.

The invention further relates to a method of producing an antibody or antiserum comprising the steps of providing the compound of Formula 1, inoculating an animal or humans with said compound to stimulate an immune response to said compound, withdrawing serum from said animal and optionally purifying said serum to obtain the antibody or antiserum. The resulting antibody or antiserum binds to *Campylobacter* species wherein the glycan described herein is native thereto, including *Campylobacter fetus venerealis, Campylobacter fetus fetus, Campylobacter concisus, Campylobacter hyointestinalis* and *Campylobacter hyointestinalis* subspecies, *Campylobacter sputorum* and *Campylobacter sputorum* subspecies, *Campylobacter tanienae, Campylobacter ureolyticus, Campylobacter hominis, Campylobacter gracilis, Campylobacter rectus, Campylobacter showae, Campylobacter mucosalis* and *Campylobacter curvus*.

The antibody or antiserum can be used for diagnostic purposes, to detect the presence of said organisms in an animal or in a human.

Compounds of the present invention may be used in a vaccine formulation, with or without an adjuvant, against *Campylobacter fetus venerealis*, which is a major cause of reproductive failure in cattle and for which the current vaccine is of limited use, or against other *Campylobacter* species wherein the glycan of Formula 1 is native to such organism, including the species listed above. Compounds of the present invention have possible uses in protein glycoprotein engineering, therapeutic and diagnostic applications. The invention thus relates to a vaccine comprising the compound of Formula 1, optionally connected or linked to a single amino acid, an oligopeptide, a peptide, a protein, or a lipid. The single amino acid may comprise asparagine.

The invention further relates to the use of said vaccine to treat or prevent an infection caused by a *Campylobacter* organism, wherein the compound of Formula 1 comprises a native glycan within said organism, and a method of treatment comprising said use, within a human or animal.

According to another aspect, the invention relates to a method of improving the productivity and health of an animal herd by administering to said herd the vaccine as described above.

The vaccines, antibodies and antisera described herein may also be used to for prevention, treatment and diagnosis in humans.

DETAILED DESCRIPTION

The present invention relates to the glycan compound A-GlcNAc[GlcNAc]-GalNAc-GalNAc-QuiNAc4NAc, wherein A is GlcNAc or Glc. The above compound encompasses the two glycan compounds GlcNAc-GlcNAc

[GlcNAc]-GalNAc-GalNAc-QuiNAc4NAc (herein Formula 1A) and Glc-GlcNAc[GlcNAc]-GalNAc-GalNAc-QuiNAc4NAc (herein Formula 1B).

In the above Formulae, QuiNAc4NAc represents an alternative signifier of the saccharide Bac, which constitutes an abbreviation of bacillosamine (also known as diNAcBac). The compound of Formula 1 is optionally connected or linked to a single amino acid, an oligopeptide, a peptide, a protein, or a lipid.

Said lipid can be isolated and purified from a bacterial, archaeal or eukaryotic source or can be chemically synthesized. Said linkage of the glycan compound to the lipid can be mediated by a phosphate, a pyrophosphate linker or by a glycosidic linkage. Examples of lipids (with various chain lengths, saturation grade and configuration) linked to N-glycans were described (Faridmoayer et al., Journal of Biological Chemistry, 2009; Chen M M et al., Biochemistry, 2007). Lipid-linked N-glycan compounds produced in the native host or in a heterologous expression system include undecaprenyl-phosphate-linked N-glycan compounds as shown for the *C. jejuni* N-glycan (Reid C W et al., Analytical Chemistry, 2008, Reid C W et al., Analytical Chemistry, 2009) and proposed for the *C. lari* N-glycan (Schwarz F et al., Glycobiology 2011)) and N-glycan-LipidA conjugates (shown for the N-glycan of *C. jejuni* (van Sorge N M et al., Cellular Microbiology, 2009)).

It has been determined that the above compound is substantially conserved across multiple species of *Campylobacter*.

FIGS. 3A-3D depict N-glycans and fOS in select *Campylobacter* species. (A) Western Blot using antiserum that recognizes the N-linked hepta-saccharide of *C. jejuni* cross-reacted with other *Campylobacter* species (open boxes) that also reacted with (B) soybean agglutinin recognizing terminal GalNAc residues, but shows little reactivity with (C) wheat-germ agglutinin (WGA) that recognizes terminal GlcNAc residues present in Formula 1A and Formula 1B. Species that did not react with the *C. jejuni*-specific antiserum but reacted with WGA were highlighted. (D) Examples of mass spectrometry of fractions enriched for fOS or Asn-linked of (1) *C. jejuni* (2) *C. fetus venerealis*, (3) *C. concisus*, (4) *C. fetus fetus*, and (5) *C. hyointestinalis*; results of all species analyzed by mass spectrometry are summarized in Table 1.

TABLE 1

Figure 1:
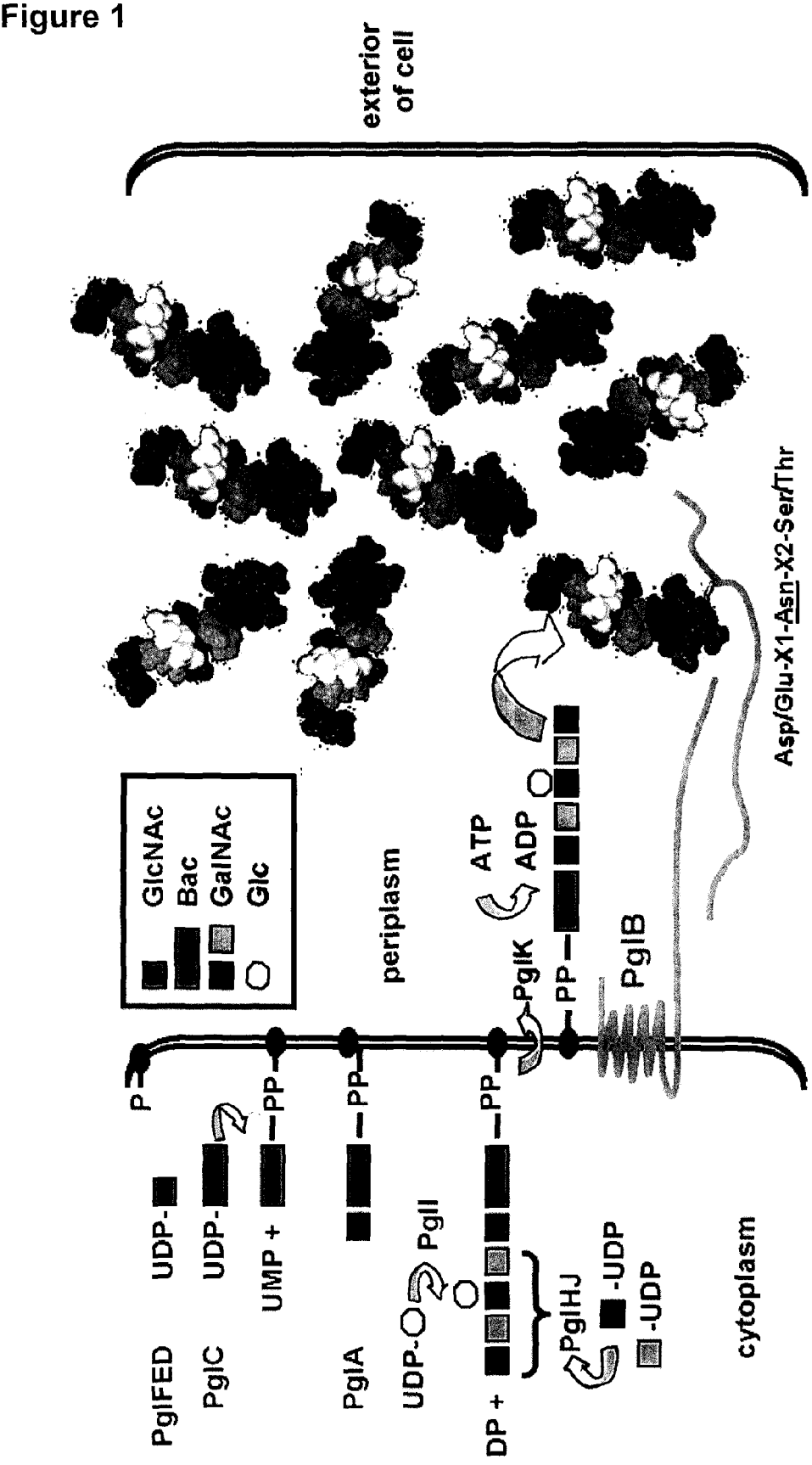
FIG. 1 shows N-linked protein glycosylation and free oligosaccharides in *C. jejuni*.
Figure 2:
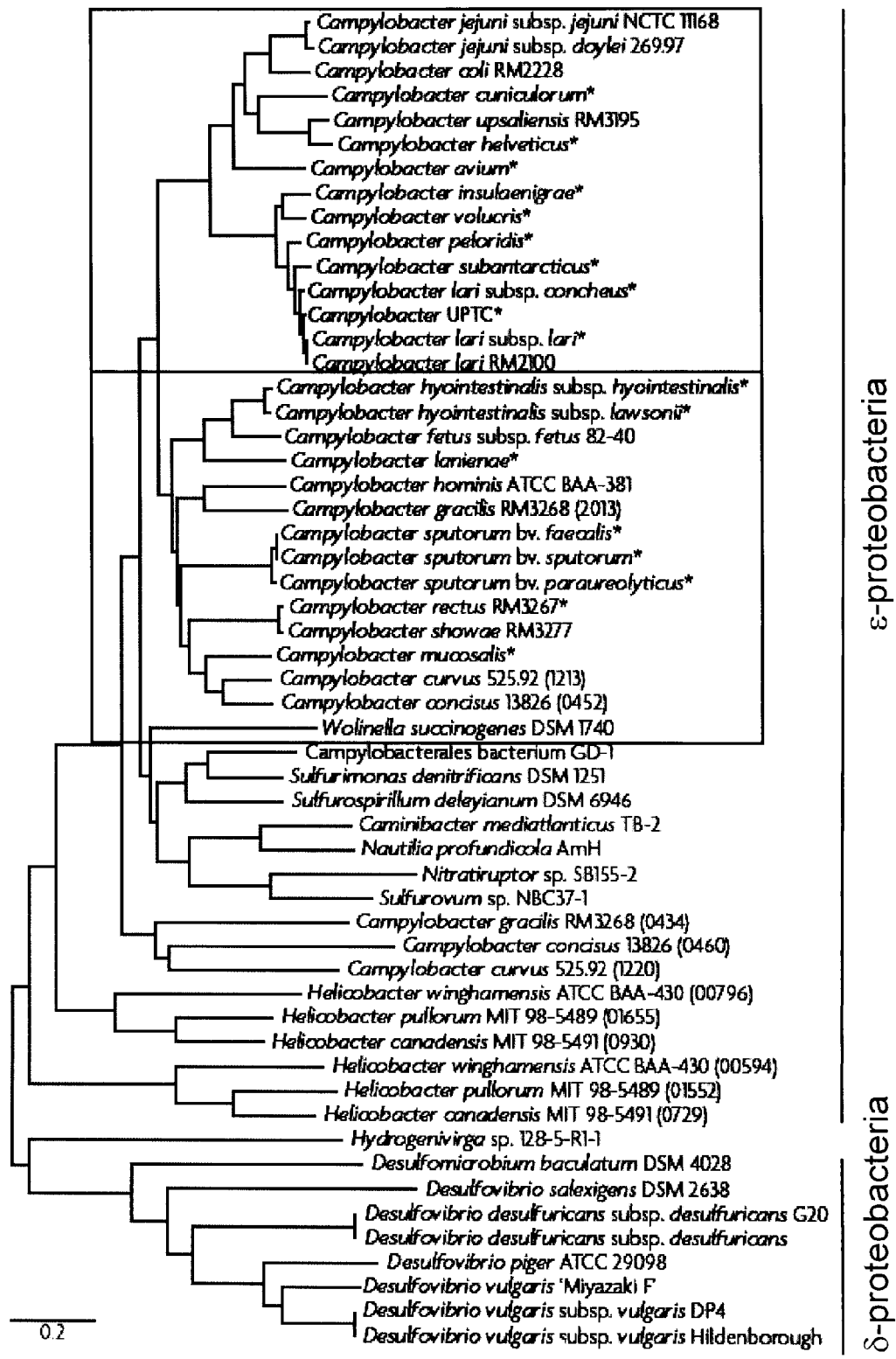
FIG. 2 is a chart summarizing the fOS and N-glycan structures in various *Campylobacter* species.
Figure 3:
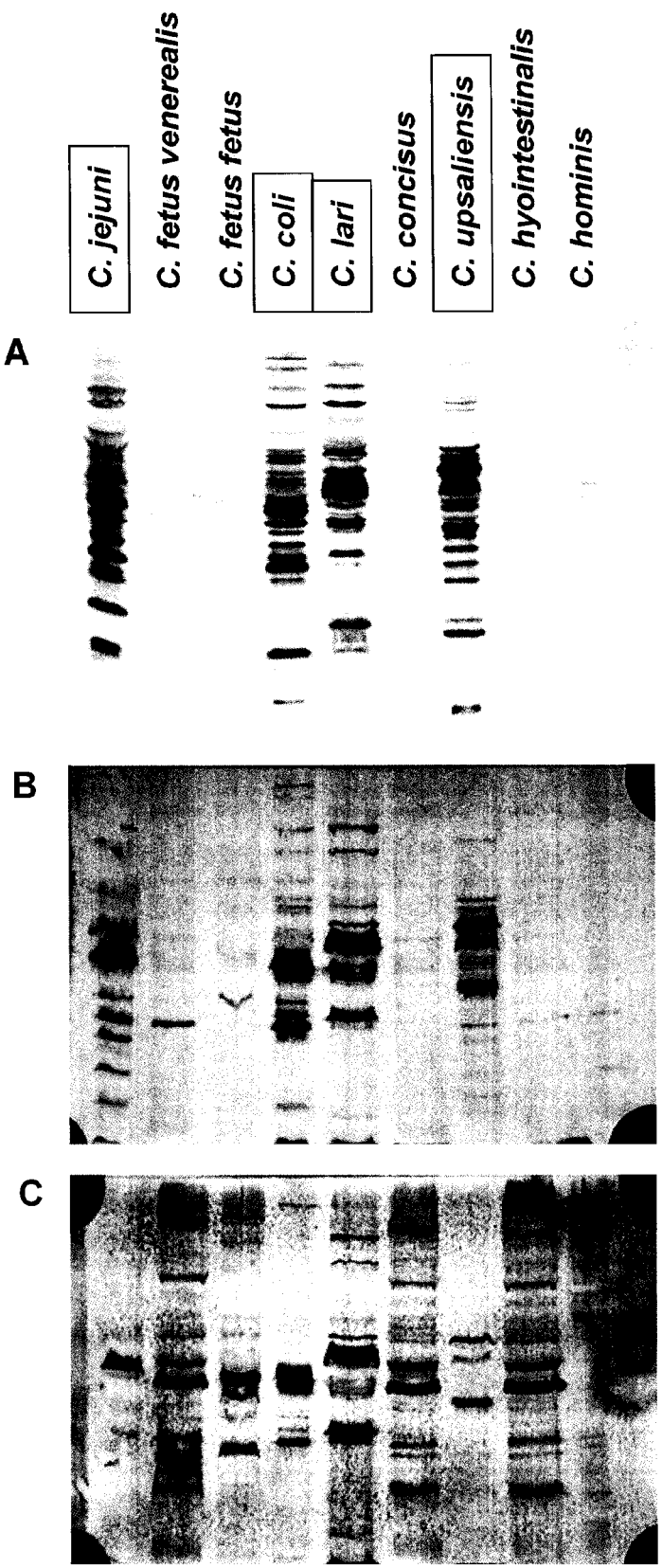
FIGS. 3A-3D depict N-glycans and fOS analyses in select *Campylobacter* species.
Figure 4:
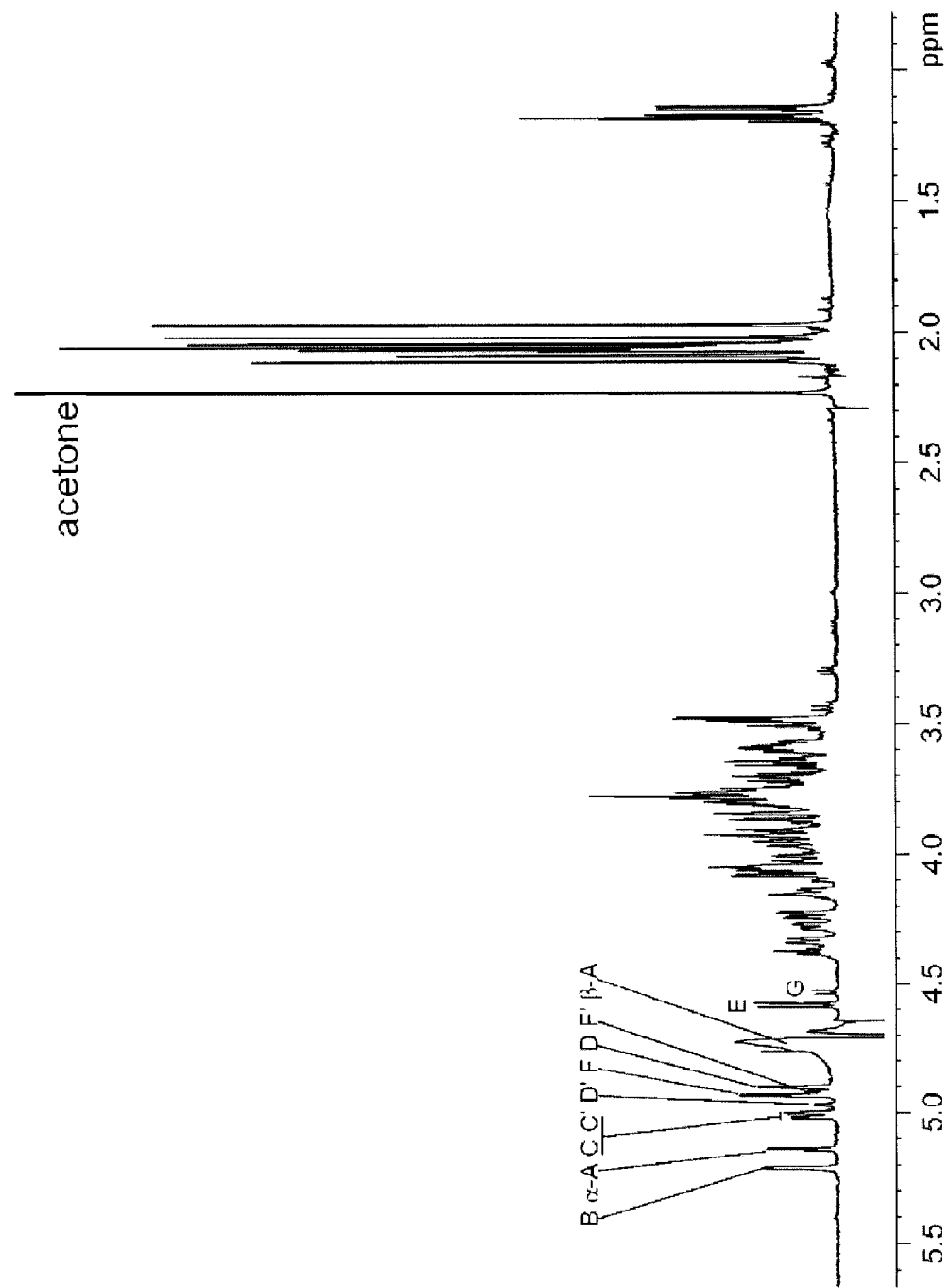
FIG. 4A is the 1H NMR spectrum of purified fOS from *C. fetus fetus*.
FIG. 4B overlay of 2D HSQC NMR spectra for *C. fetus fetus* and *C. fetus venerealis*.
Figure 4:
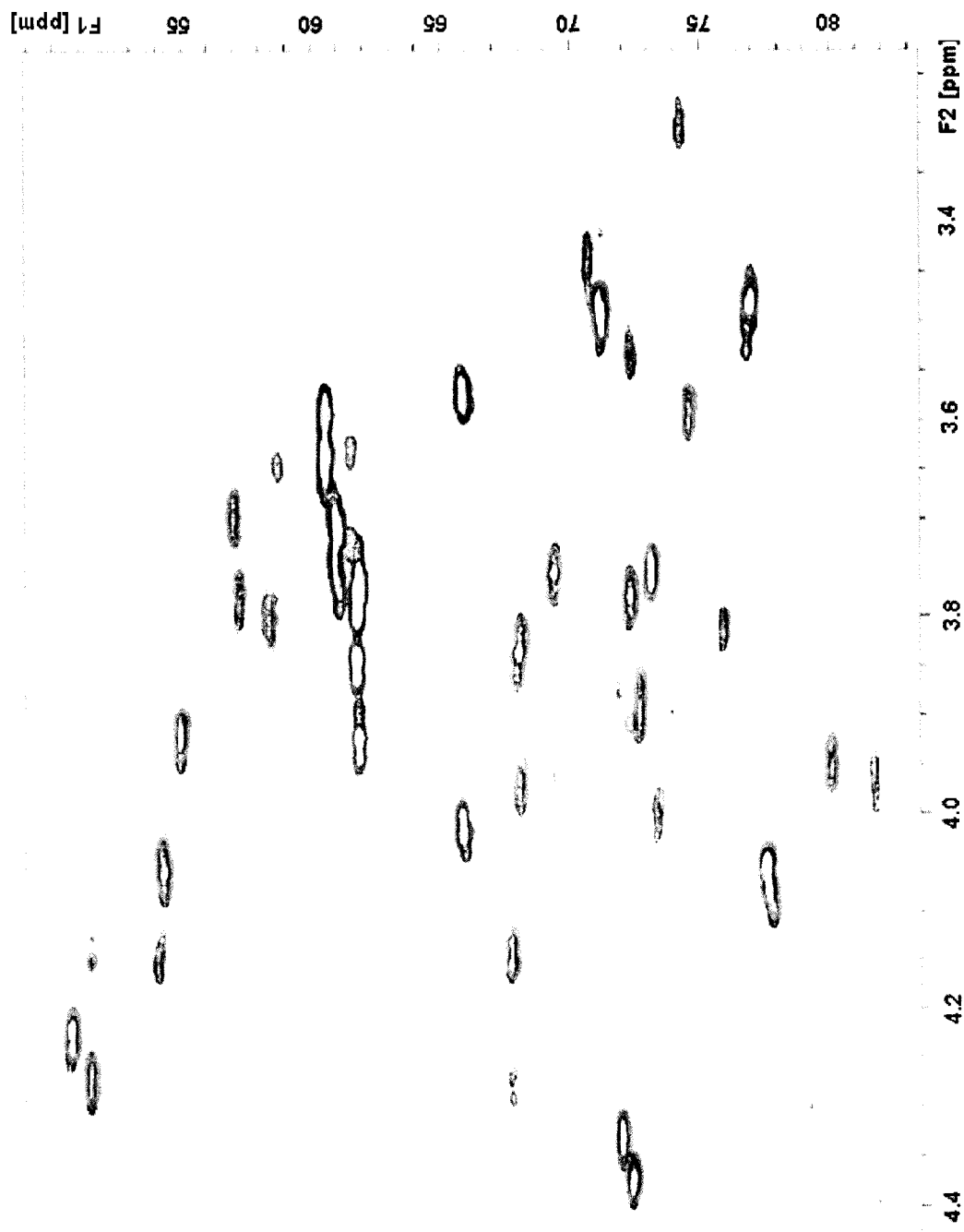

Table 1. fOS and N-glycan structure masses determined by mass spectrometry in select *Campylobacter* strains. Numbers indicate the mass(es) of Formula 1A and Formula 1B either as free oligosaccharide (fOS) or Asn-linked. Masses were obtained in positive ion mode from whole cell lysates of the indicated strain. The structures of Formula 1A and Formula 1B were determined by NMR as shown in FIG. 4, Table 3 and FIG. 5. N/D, not determined.

| Campylobacter species | MS-MS$^2$ (m/z) free oligosaccharide (fOS) | N-linked glycan |
|---|---|---|
| *C. jejuni* | GalNAc5-Glc-Bac (1425.0) | HexNAc5-Hex-Bac-Asn (1539.5) |
| *C. coli* | HexNAc5-Hex-Bac (1425.0) | N/D |
| *C. upsaliensis* | HexNAc5-Hex-Bac (1425.0) | N/D |
| *C. fetus fetus* | HexNAc5-Bac (1263.5) Formula 1A HexNAc4-Glc-Bac (1222.5) Formula 1B | HexNAc5-Bac-Asn (1377.5) Formula 1A-Asn(N)-linked On a Peptide: HexNAc5-Bac-Asn Formula 1A-Asn(N)-linked Hex-HexNAc4-Bac-Asn Formula 1B-Asn(N)-linked |
| *C. fetus venerealis* | HexNAc5-Bac (1263.5) Formula 1A HexNAc4-Hex-Bac (1222.5) Formula 1B | On a Peptide: HexNAc5-Bac-Asn Formula 1A-Asn(N)-linked Hex-HexNAc4-Bac-Asn Formula 1B-Asn(N)-linked |
| *C. concisus* | HexNAc5-Bac (1263.5) Formula 1A HexNAc4-Hex-Bac (1222.0) Formula 1B | On a Peptide: HexNAc5-Bac-Asn Formula 1A-Asn(N)-linked Hex-HexNAc4-Bac-Asn Formula 1B-Asn(N)-linked |
| *C. hyointestinalis* | HexNAc5-Bac (1263.5) Formula 1A HexNAc4-Hex-Bac (1222.0) Formula 1B | N/D |

Example 1

Purification of Compounds of Formulae 1A and 1B

*Campylobacter jejuni* 11168, *C. concisus*, *C. hyointestinalis*, *C. fetus fetus* and *C. fetus venerealis* were grown under microaerobic conditions. Whole cells obtained after centrifugation were digested with large excess of proteinase K at pH 8 (adjusted by addition of ammonia) at 37° C. for 48 hours. Products of digestion or free oligosaccharides were separated on Sephadex G-15 column (1.5×60 cm) and each fraction eluted before the salt peak was dried and analyzed by $^1$H NMR. Fractions containing desired products were separated by anion exchange chromatography on a Hitrap Q column (5 mL size, Amersham) and the glycans were eluted with a linear gradient of NaCl—(0-1 M, 1 h) that resulted in the isolation of a mixture of both glycan compounds (Formula 1A and Formula 1B). Desalting was performed on Sephadex G15 prior to analysis by NMR.

Example 2

NMR Spectroscopy Analysis

Figure 5:
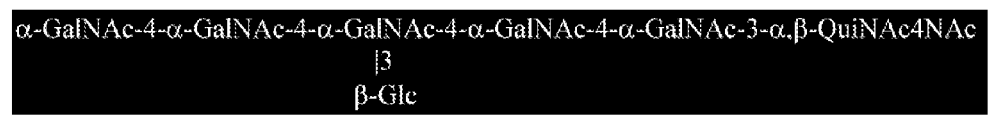
FIGS. 5A to 5C depict structures of fOS and N-glycans of *C. jejuni, C. coli* and *C. upsaliensis* (Structure 1) and Formula 1A and Formula 1B from the other *Campylobacter* species described herein.
Figure 5:
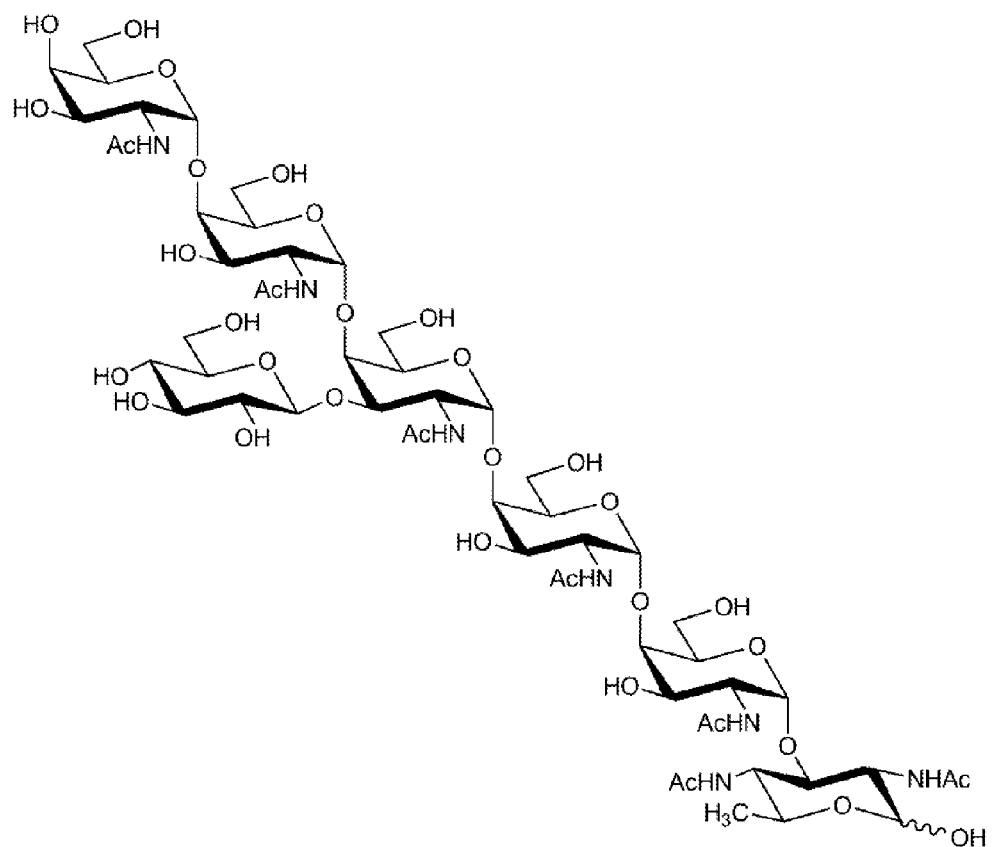
Figure 5:
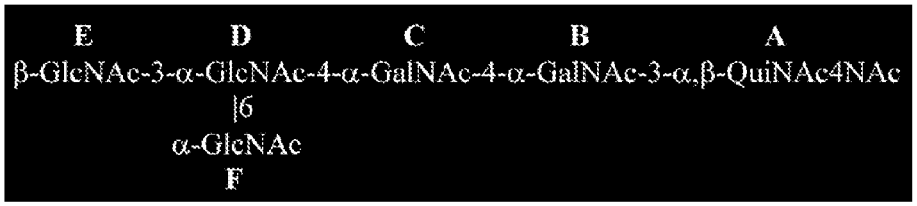
Figure 5:
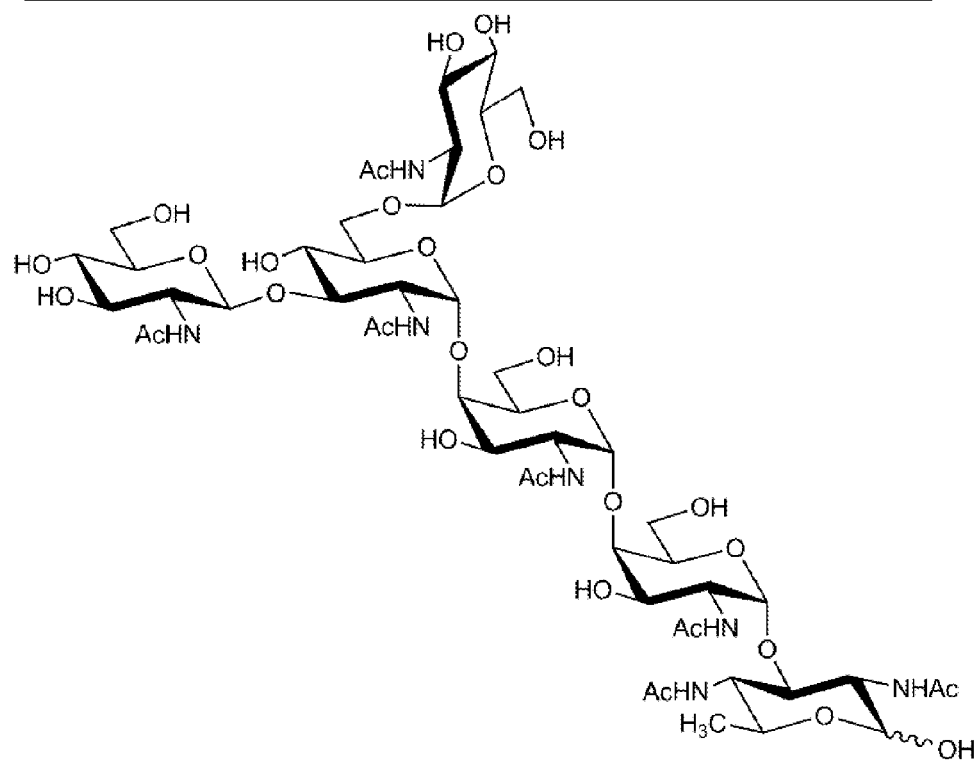
Figure 5C:
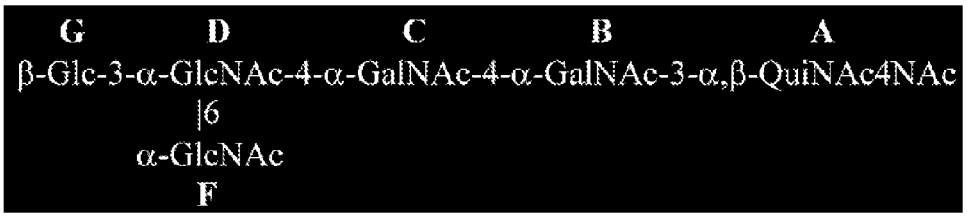

NMR experiments on the glycans obtained in example 1 were carried out on a Varian INOVA 500 MHz ($^1$H) spectrometer with 3 mm gradient probe at 25° C. with acetone internal reference (2.225 ppm for $^1$H and 31.45 ppm for $^{13}$C) using standard pulse sequences DQCOSY, TOCSY (mixing time 120 ms), ROESY (mixing time 500 ms), HSQC and HMBC (100 ms long range transfer delay). AQ time was kept at 0.8-1 sec for H-H correlations and 0.25 sec for HSQC, 256 increments was acquired for t1. The Results are shown in FIG. 4, FIG. 5 (NMR spectra and structures) and Table 2, corresponding chemical shifts.

FIG. 4A is the 1H NMR spectrum of purified fOS from *C. fetus fetus*. FIG. 4B overlay of 2D HSQC spectra for *C. fetus fetus* and *C. fetus venerealis* indicating that fOS structures from both species are identical. The NMR spectrum can also be overlaid with one obtained for *C. concisus* (not shown).

The corresponding chemical shifts δ(ppm) for the purified free oligosaccharide from *C. fetus fetus* (as shown in FIG. 4 A) are summarized in Table 2. Carbon and proton chemical shifts were referenced to an internal acetone standard (δH 2.225 ppm, δC 31.07 ppm).

The *campylobacter* glycans that are either added to protein or appear in a free form (fOS) can be divided into two structural groups. The first group of *Campylobacter* species produces a unique glycan structure that was previously determined for C, *jejuni* and *C. coli* and herein for *C. upsaliensis*. Campylobacters which fall into the second group consist of *Campylobacter fetus venerealis* (cause of venereal disease and infertility in cattle), *Campylobacter fetus fetus* (cause of sheep abortions), *Campylobacter concisus, Campylobacter hyointestinalis, Campylobacter hyointestinalis* subspecies, *Campylobacter sputorum* and *Campylobacter sputorum* subspecies, *Campylobacter lanienae, Campylobacter ureolyticus, Campylobacter hominis, Campylobacter gracilis, Campylobacter rectus, Campylobacter showae, Campylobacter mucosalis* and *Campylobacter curvus.*

Structure determination by NMR using large scale purified free oligosaccharides (fOS) from *C. fetus fetus, C. fetus venerealis*, and *C. concisus* demonstrated that this second group of campylobacters produced a structure different from that originally described for *C. jejuni* and *C. coli* (FIG. 4 and FIGS. 5A-5C).

TABLE 2

| Unit, compound | Atom | 1 | 2 | 3 | 4 | 5 | 6(6a) | 6b |
|---|---|---|---|---|---|---|---|---|
| α-QuiNAc4NAc α-A | $^1$H | 5.14 | 4.07 | 4.00 | 3.80 | 3.97 | 1.14 | |
| | $^{13}$C | 92.2 | 54.3 | 73.3 | 58.3 | 68.0 | 17.6 | |
| α-QuiNAc4NAc β-A | $^1$H | 4.73 | 3.78 | 3.81 | 3.80 | 3.54 | 1.17 | |
| | $^{13}$C | 95.6 | 57.2 | 75.9 | 58.3 | 72.3 | 17.6 | |
| α-GalNAc B | $^1$H | 5.21 | 4.23 | 3.83 | 4.05 | 3.89 | 3.70 | 3.75 |
| | $^{13}$C | 98.0 | 50.7 | 68.0 | 77.5 | 72.6 | 60.9 | |
| α-GalNAc C | $^1$H | 5.00<br>5.02 | 4.28 | 4.14 | 4.08 | 4.37 | 3.59 | 3.64 |
| | $^{13}$C | 99.4 | 51.4 | 67.7 | 77.6 | 72.3 | 60.5 | |
| α-GlcNAc D | $^1$H | 4.90 | 4.05 | 3.95 | 3.76 | 4.33 | 3.57 | 4.01 |
| | $^{13}$C | 99.4 | 54.2 | 80.0 | 69.3 | 71.9 | 65.8 | |
| β-GlcNAc E | $^1$H | 4.58 | 3.70 | 3.59 | 3.48 | 3.48 | 3.77 | 3.93 |
| | $^{13}$C | 102.5 | 57.0 | 74.6 | 71.1 | 77.0 | 61.8 | |
| α-GlcNAc F | $^1$H | 4.93 | 3.92 | 3.78 | 3.50 | 3.75 | 3.79 | 3.85 |
| | $^{13}$C | 98.1 | 54.9 | 72.3 | 71.2 | 73.1 | 61.7 | |
| α-GalNAc C' | $^1$H | 5.00 | 4.28 | 4.14 | 4.10 | 4.37 | 3.59 | 3.64 |
| | $^{13}$C | 99.4 | 51.4 | 67.7 | 77.7 | 72.3 | 60.5 | |
| α-GlcNAc D' | $^1$H | 4.97 | 4.16 | 3.97 | 3.75 | 4.34 | 3.57 | 4.01 |
| | $^{13}$C | 99.5 | 54.1 | 81.7 | 69.3 | 71.9 | 65.8 | |
| β-Glc G | $^1$H | 4.53 | 3.29 | 3.51 | 3.42 | 3.48 | 3.74 | 3.91 |
| | $^{13}$C | 104.3 | 74.2 | 76.8 | 70.6 | 76.8 | 61.7 | |

Table 2: Chemical shifts δ(ppm) for the purified free oligosaccharides (Formula 1A and Formula 1B) from *C. fetus fetus* (for the spectrum shown in FIG. 4A). Carbon and proton chemical shifts were referenced to an internal acetone standard (δH 2.225 ppm, δC 31.07 ppm). Capital letters refer to the single sugar residues as outlined in FIGS. 4A and 5.

Example 3

Preparation of Glycan of Formula 1 Compounds Linked to Single Amino Acid

A Pronase E digest of whole cell extracts obtained after lysis of intact cells followed by mass spectrometry as described by Liu X. et al., AnalChem, 2005 and Nothaft H. et al., Methods Mol Biol, 2010 identified the *C. jejuni* heptasaccharide (structure 1) attached to a single asparagine and Formula 1A linked to a single asparagine in *C. fetus fetus* (Table 1).

Example 4

Expression of Formula 1 Compounds

Figure 6:
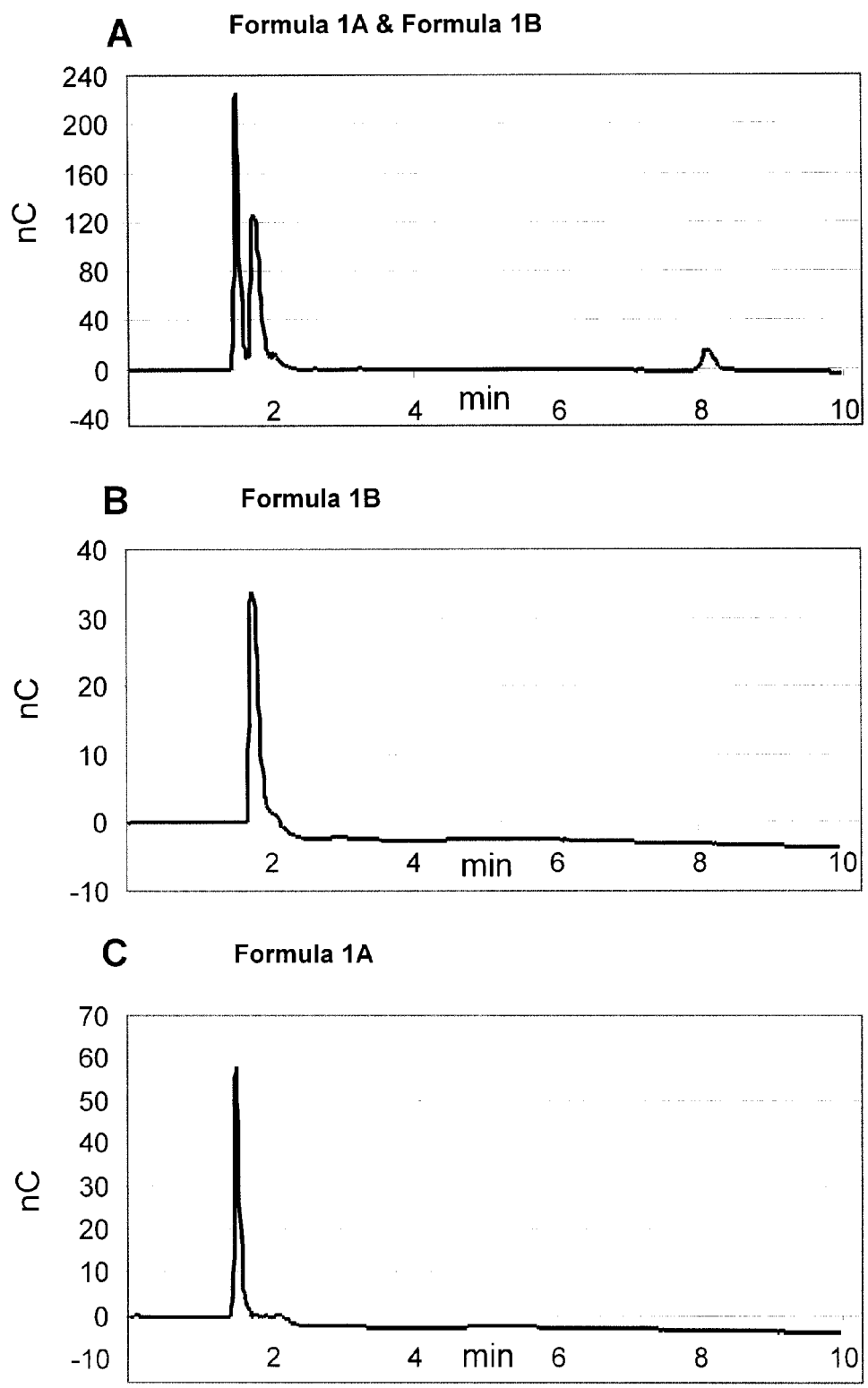
FIG. 6 shows elution profiles of Formula 1A and Formula 1B, under conditions described herein and the confirmation of purified Formula 1A and Formula 1B.
Figure 6:
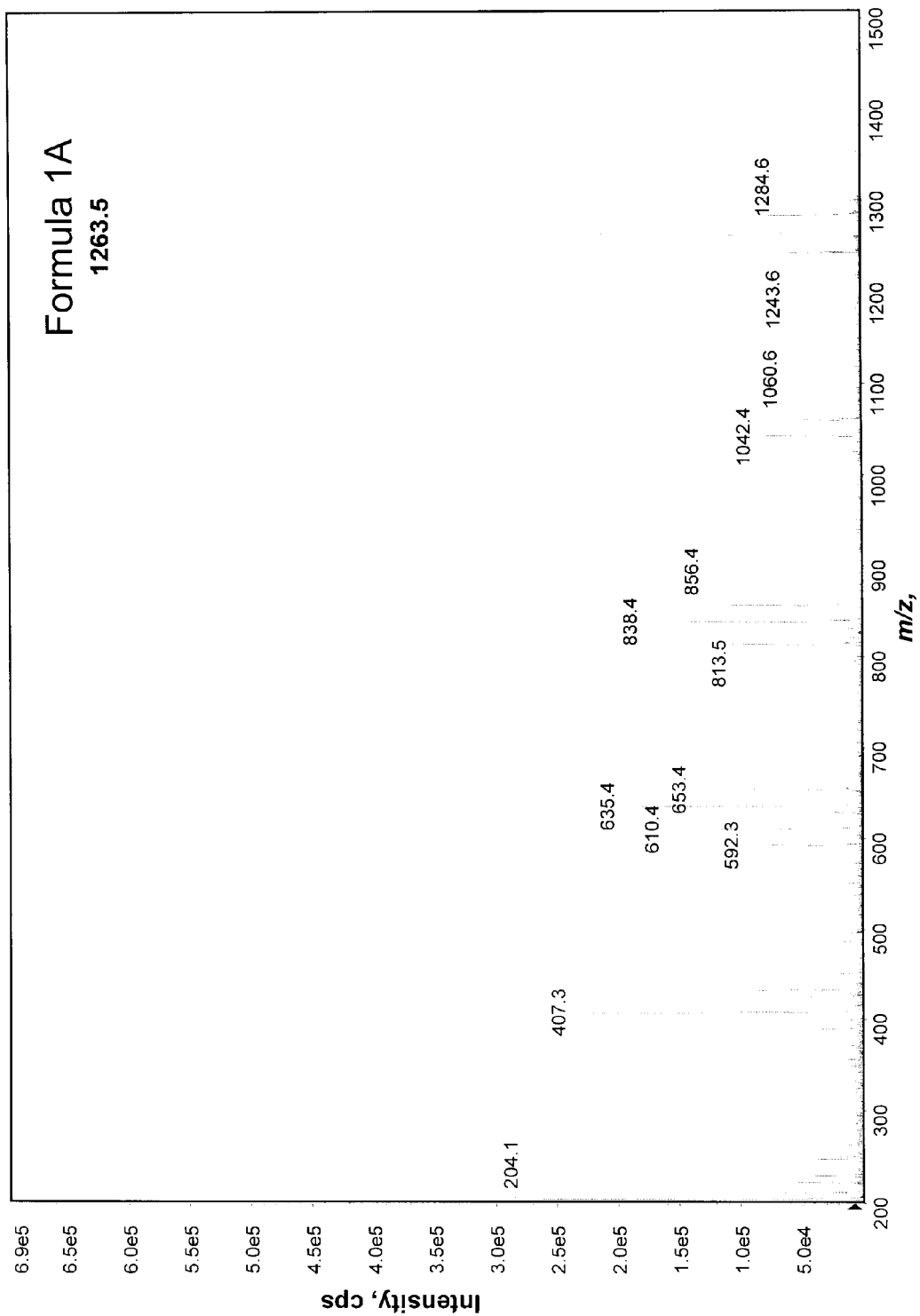
Figure 6E:
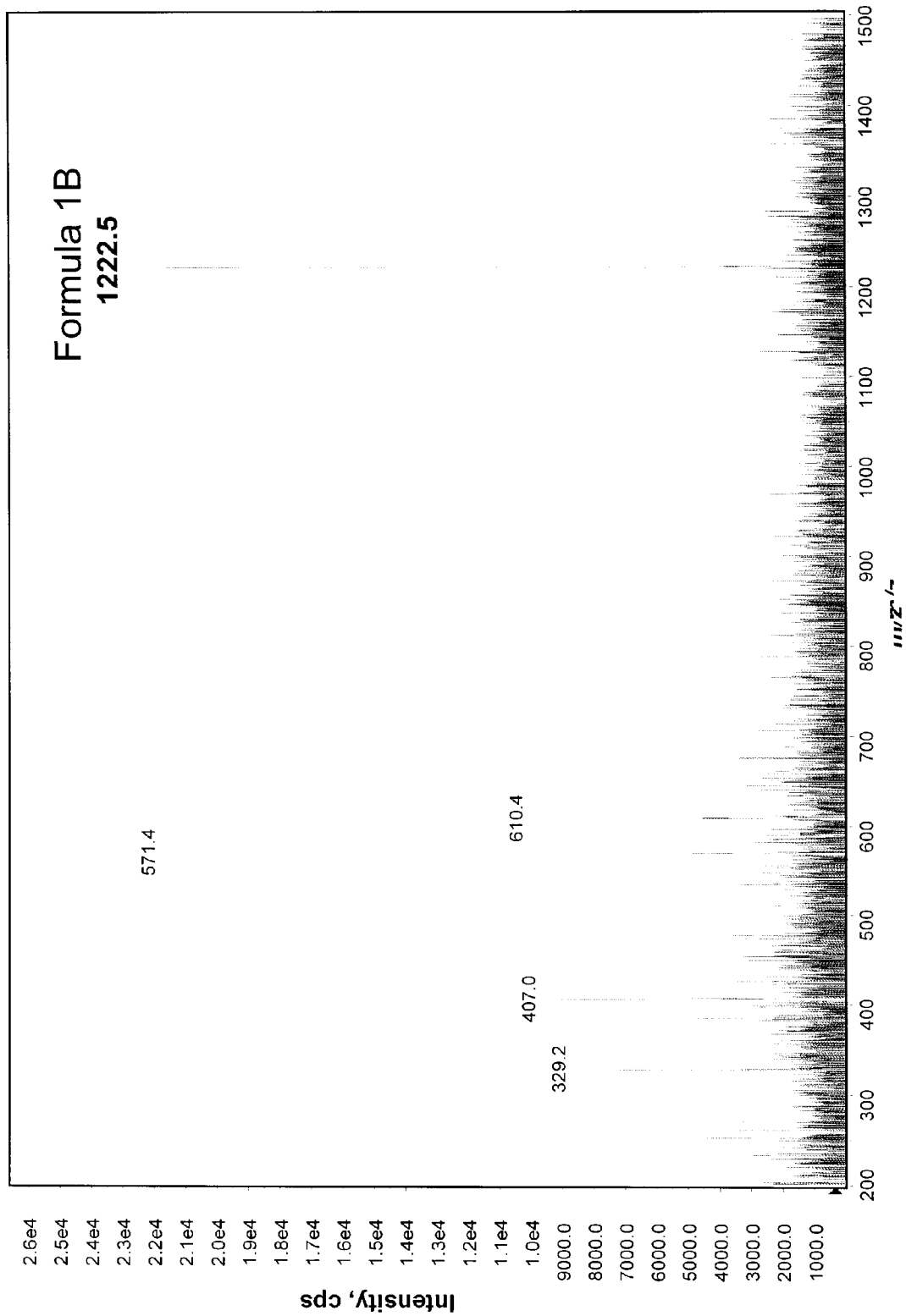

The protein glycosylation operon encoding all the genes necessary for the production and transfer of Formula 1A and Formula 1B compounds can be cloned and expressed from an *E. coli* plasmid(s). Alternatively, the glycosyltransferases on a plasmid described by Wacker et al, Science 2002 that contains the *C. jejuni* protein glycosylation (pgl) operon can be exchanged by Formula 1A and Formula 1B producing glycosyltransferases. Expression of Formula 1A and Formula 1B compounds can be done in a heterologous system in the presence of an affinity-tagged acceptor peptide for N-linked protein glycosylation (already shown for the *C. jejuni* N-glycan and for the *C. lari* N-glycan Wacker et al., Science 2002, Schwarz et al., Glycobiology 2011) or as a fusion of such a protein with a phage protein (Duerr et al., Glycobiology, 2010). The glycan containing protein/peptide/phage can be purified by affinity-tag purification, if necessary in combination with lectin or glycan-recognizing agent affinity chromatography to separate the glycosylated and the non-glycosylated peptides.

Example 5

Purification of Formula 1A and Formula 1B

Purified Formula 1A and Formula 1B fOS were separated by high performance anion exchange chromatography with pulsed amperometric detection (HPAEC/PAD). FIG. 6 shows the elution profile of a CarboPac® PA200 Analytical Column (3×250 mm CarboPac PA100 equipped with a Guard Column: 3×50 mm) under the following conditions: flow rate: 0.5 mL/min; eluent system, 50 mM sodium acetate in 100 mM sodium hydroxide; detection mode, pulsed amperometry, quadruple waveform, Au electrode; the ambient column temperature was set to ~30° C. (FIG. 6A). Approximately 0.5 nmoles of either a mixture of Formula 1A and Formula 1B (Fig. 6B), or Formula 1B and Formula 1A after separation (FIG. 6C) using a semi preparative PA 100 column (9×250 mm) and a fraction collector (DIONEX UltiMate 3000) under the same conditions as outlined above were analyzed by HPAEC/PAD. Fractions containing either Formula 1A or Formula 1B were neutralized with equimolar amounts of 0.2 M HCl and stored at −20° C. The spectra obtained by electrospray ionization mass spectrometry (ESI-MS) of purified Formula 1A (FIG. 6D) and Formula 1B (FIG. 6E) after purification that correspond to observed masses Formula 1A and Formula 1B as outlined in Table 1.

Example 6

Conjugation of Formula 1A and Formula 1B to BSA

Purified and neutralized Formula 1A and 1B compounds prepared in Example 5 were conjugated to BSA by reductive amination (see Gildersleeve J C., Bioconjug Chem, 2008). A mixture of Bovine serum albumin (BSA; 2 µL of a 150 mg/mL solution; fraction V), sodium borate (5.5 µL of a 400 mM solution, pH 8.5), sodium sulfate (3.7 µL of a 3 M solution, 50° C.), oligosaccharide (Formula 1A or Formula 1B) (7.0 µL of 20 mM solution for 15eq), H2O (1.4 µL) and sodium cyanoborohydride (2.2 µL of a 3 M solution) was incubated in a 200 µL PCR tube in a PCR thermal cycler at 56° C. for 96 h with a heated lid. The reaction was diluted with H2O to a final volume of 100 µL, transferred to a 500 µl dialysis tube (MWCO 10,000) and dialyzed three times against H2O (2.5 L).

Figure 7:
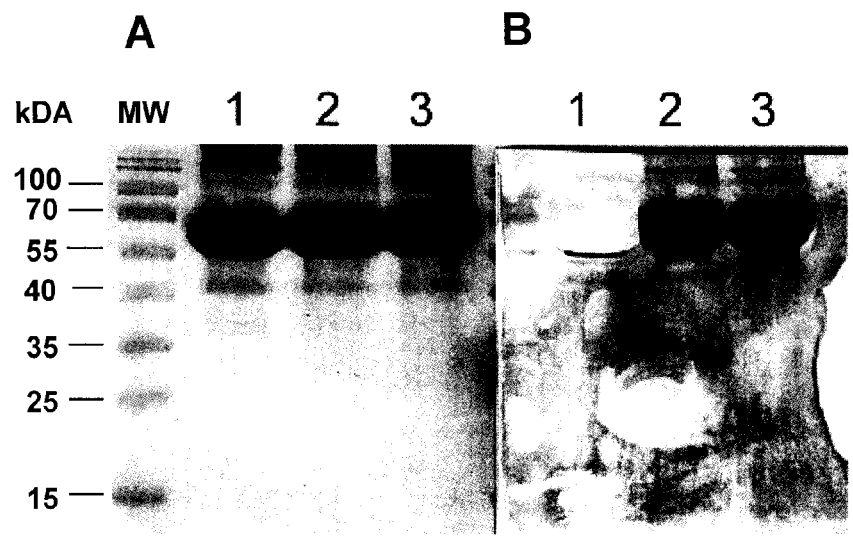
FIG. 7 illustrates conjugation of purified Formula 1A and Formula 1B compounds to BSA.

FIG. 7 shows conjugation of Formula 1A and Formula 1B to BSA: Glyco-conjugates separated by 12.5% PAGE (FIG. 7A) and monitored by Western blotting using commercially available WGA-lectin conjugated with alkaline phosphatase (FIG. 7B). Lane1, 400 ng BSA fraction V; lane 2, 400 ng of Formula 1B coupled to BSA fraction V; lane 3, 400 ng of Formula 1B coupled to BSA fraction V. Molecular weight markers (MW in KDa) are indicated on the left.

Example 7

Rabbit Immunization with Formula 1A or Formula 1B-BSA Conjugates

New Zealand White Rabbits were immunized with 2 mg of each of the glyco-conjugate compounds prepared in Example 6, using a 6 week immunization protocol (approved Animal Care Committee protocol No, 717). After an initial subcutaneous injection (at 3 sites, 0.5 ml was injected at each site) of 2.0 mg antigen using Freund's complete adjuvant (in a 1:1 ratio with the antigen), a booster dose with 2.0 mg of each Formula 1A-BSA and Formula 1B-BSA conjugates mixed with Freund's incomplete adjuvant (in a 1:1 ratio with the antigen) was given subcutaneously (at 3 sites 0.5 ml were injected at each site) after 4 weeks. After 6 weeks serum from a 5 ml blood sample from each animal was prepared by cooling the blood sample for 60 min on ice followed by centrifugation for 20 min at 10.000×g. Individual sera were analyzed for the production of Formula 1A and Formula 1B-specific antibodies by Western Blotting with *Campylobacter* whole cell lysates (FIG. 8).

Figure 8:
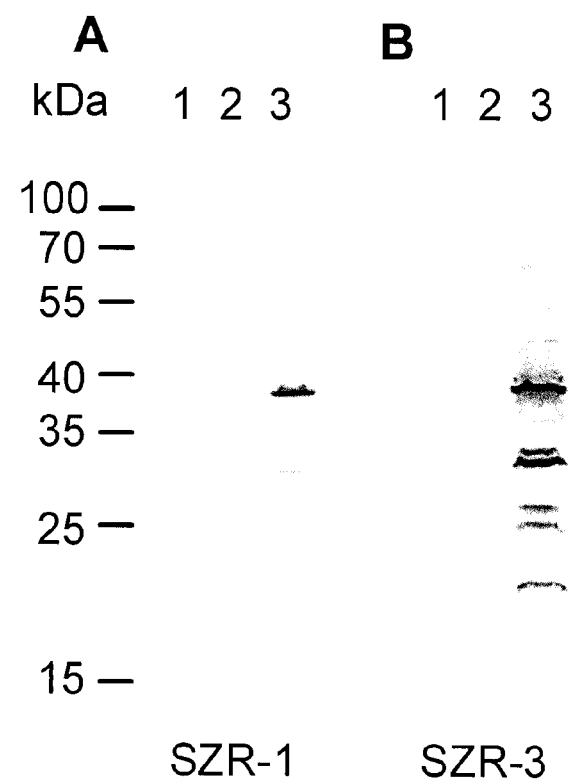
FIG. 8 illustrates immunoblots with antiserum raised against each of the BSA-glycoconjugates.
Figure 9:
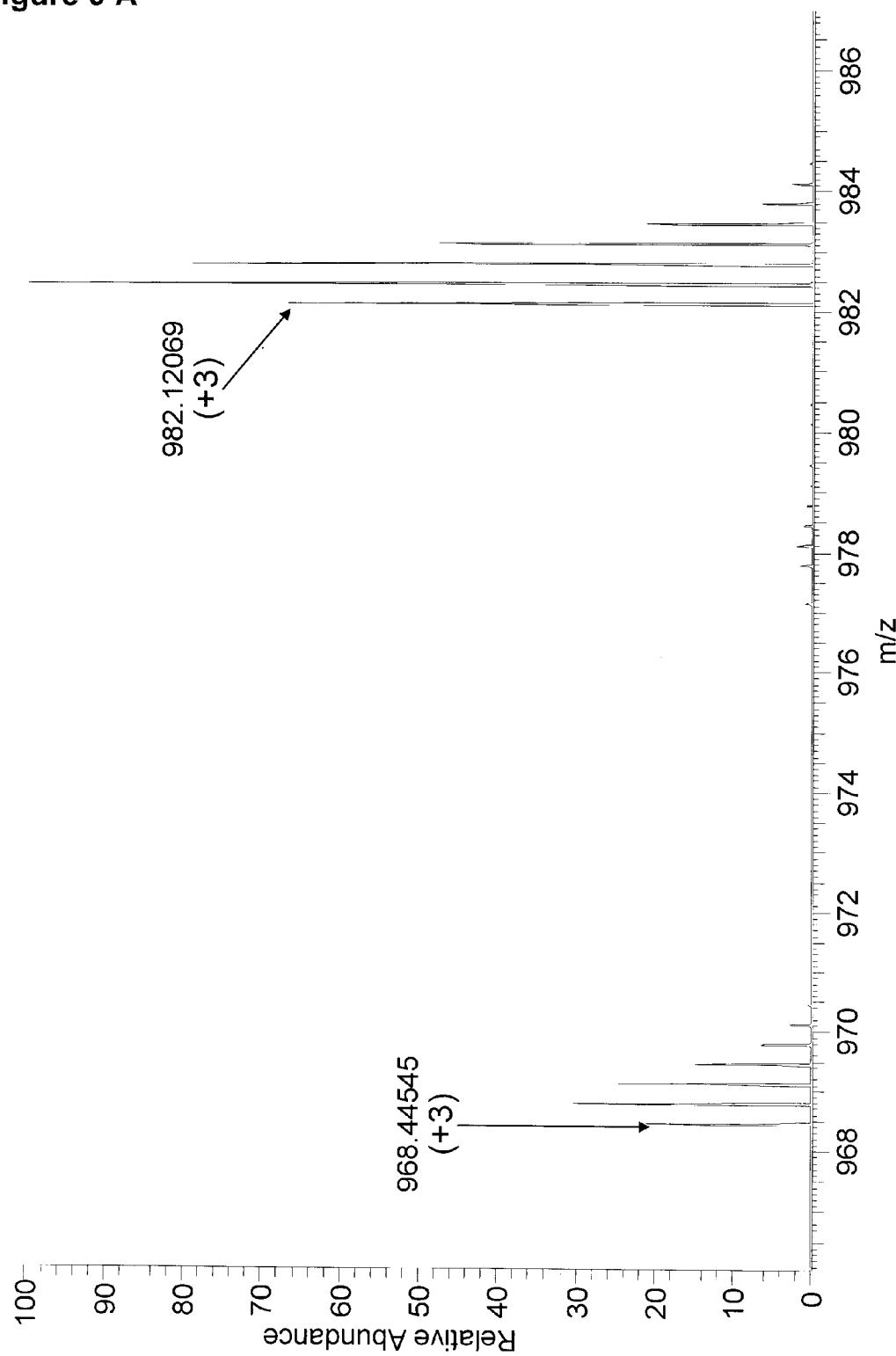
FIGS. 9A-9F depict MS spectra of glycopeptides comprising compounds of Formula 1 as the glycan moiety.
Figure 9:
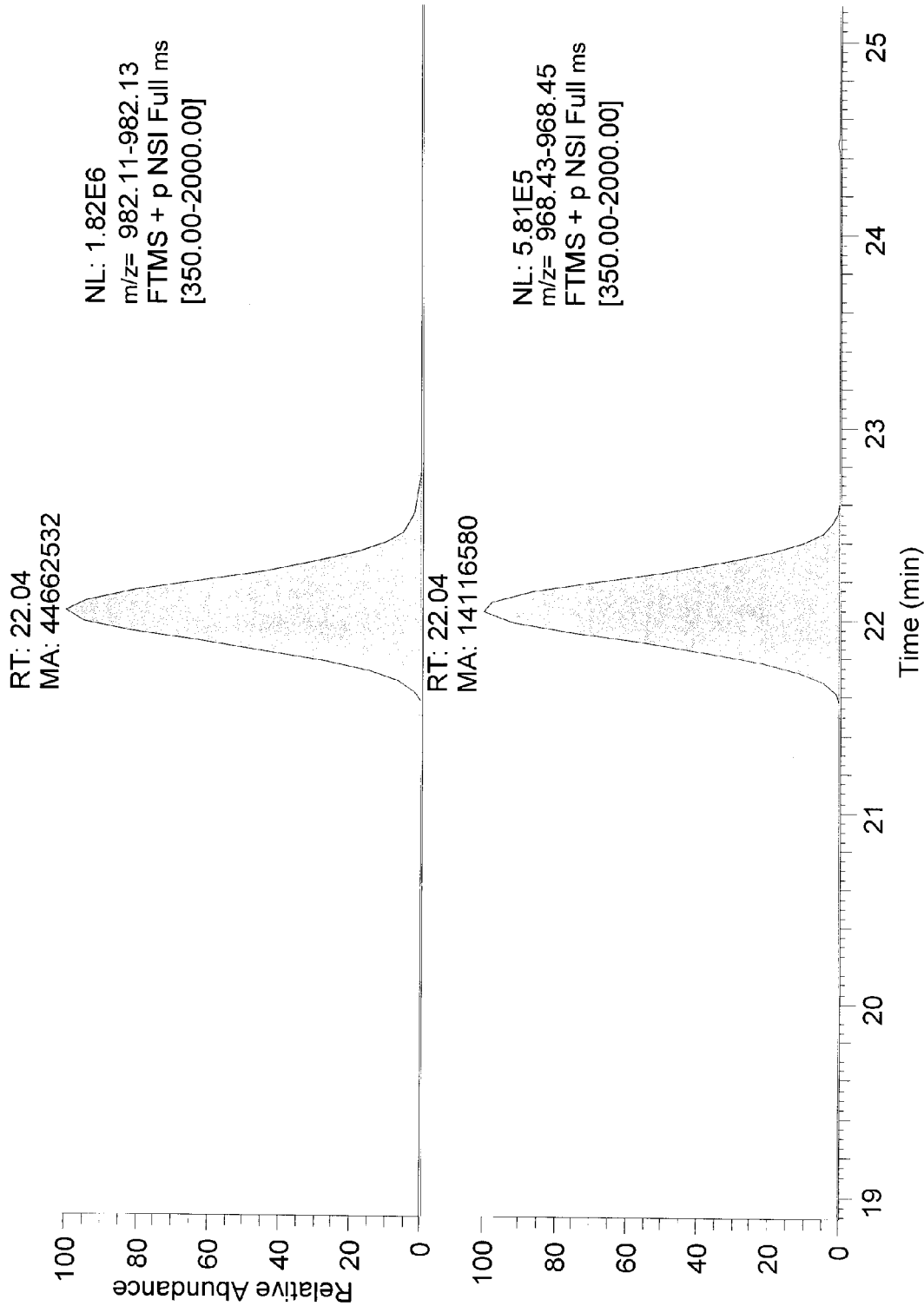
Figure 9:
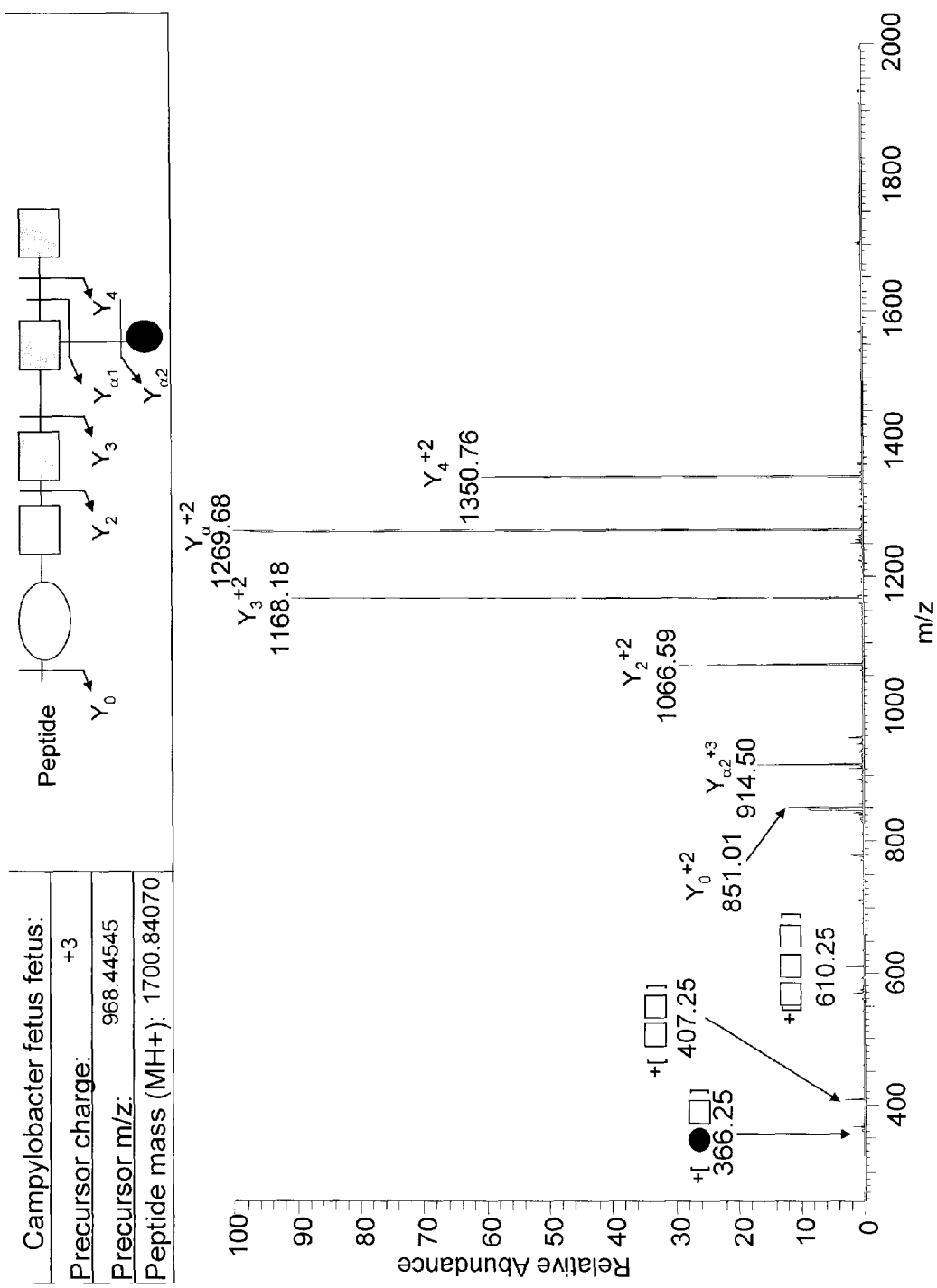
Figure 9:
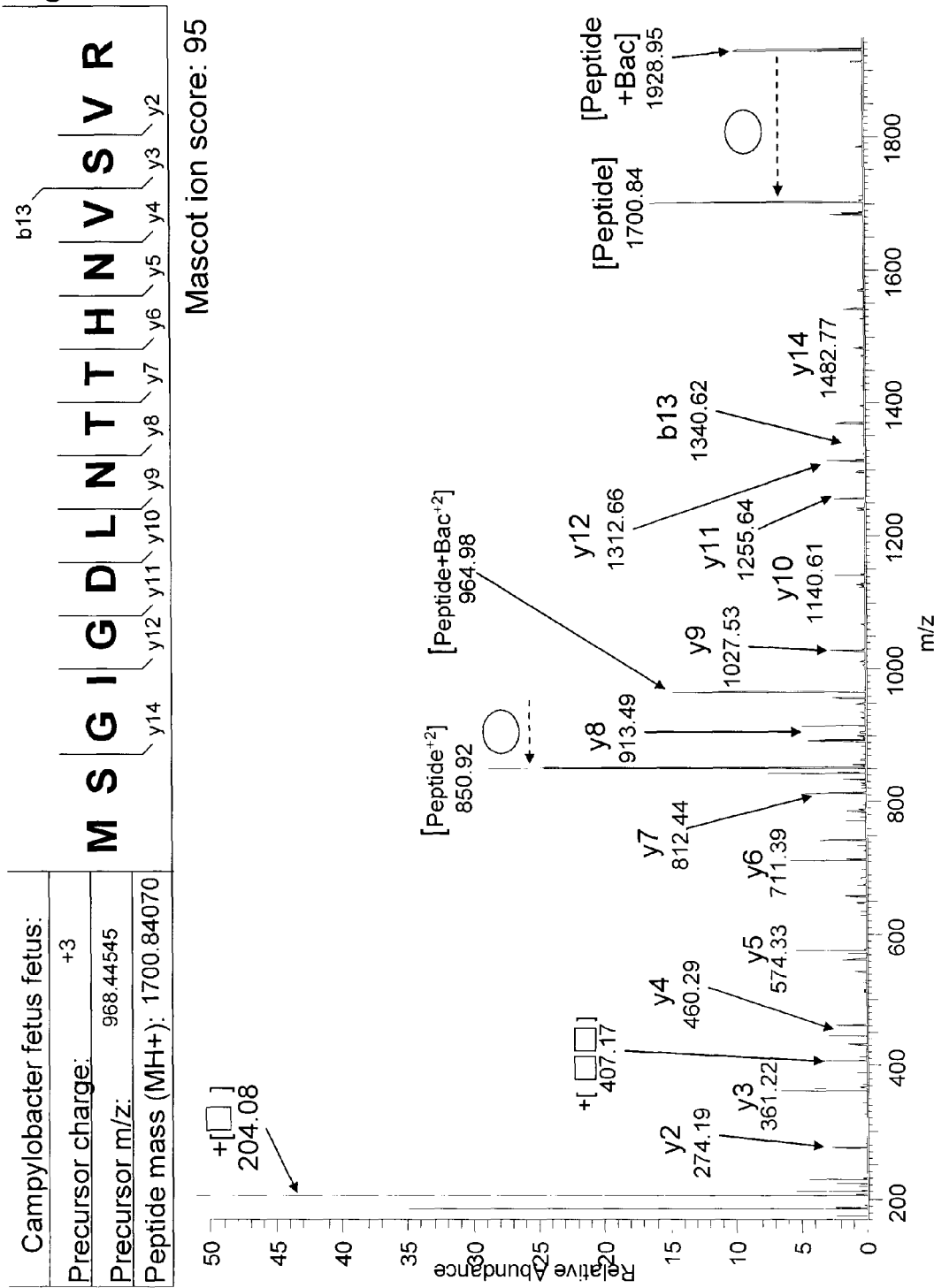
Figure 9:
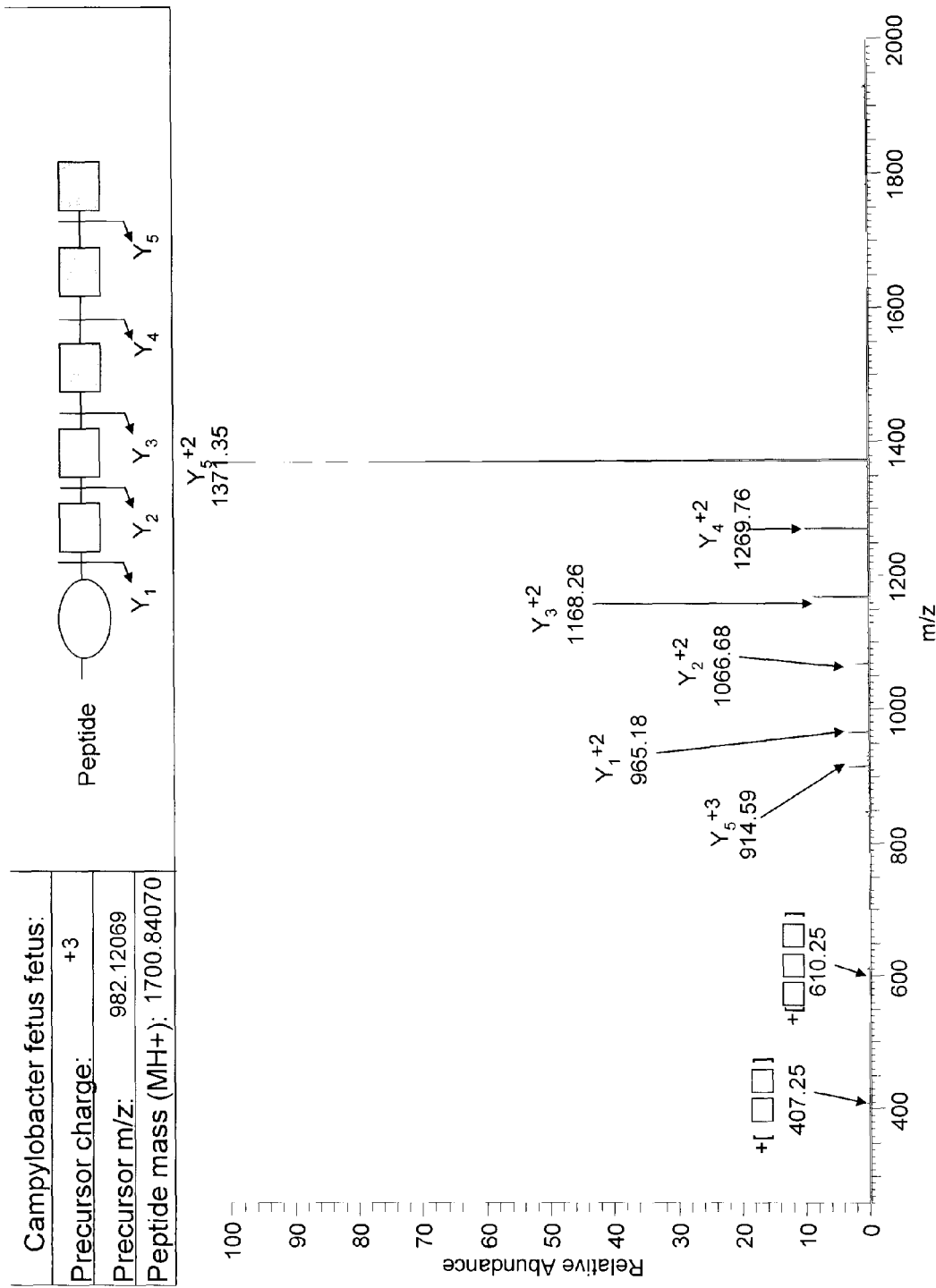
Figure 9:
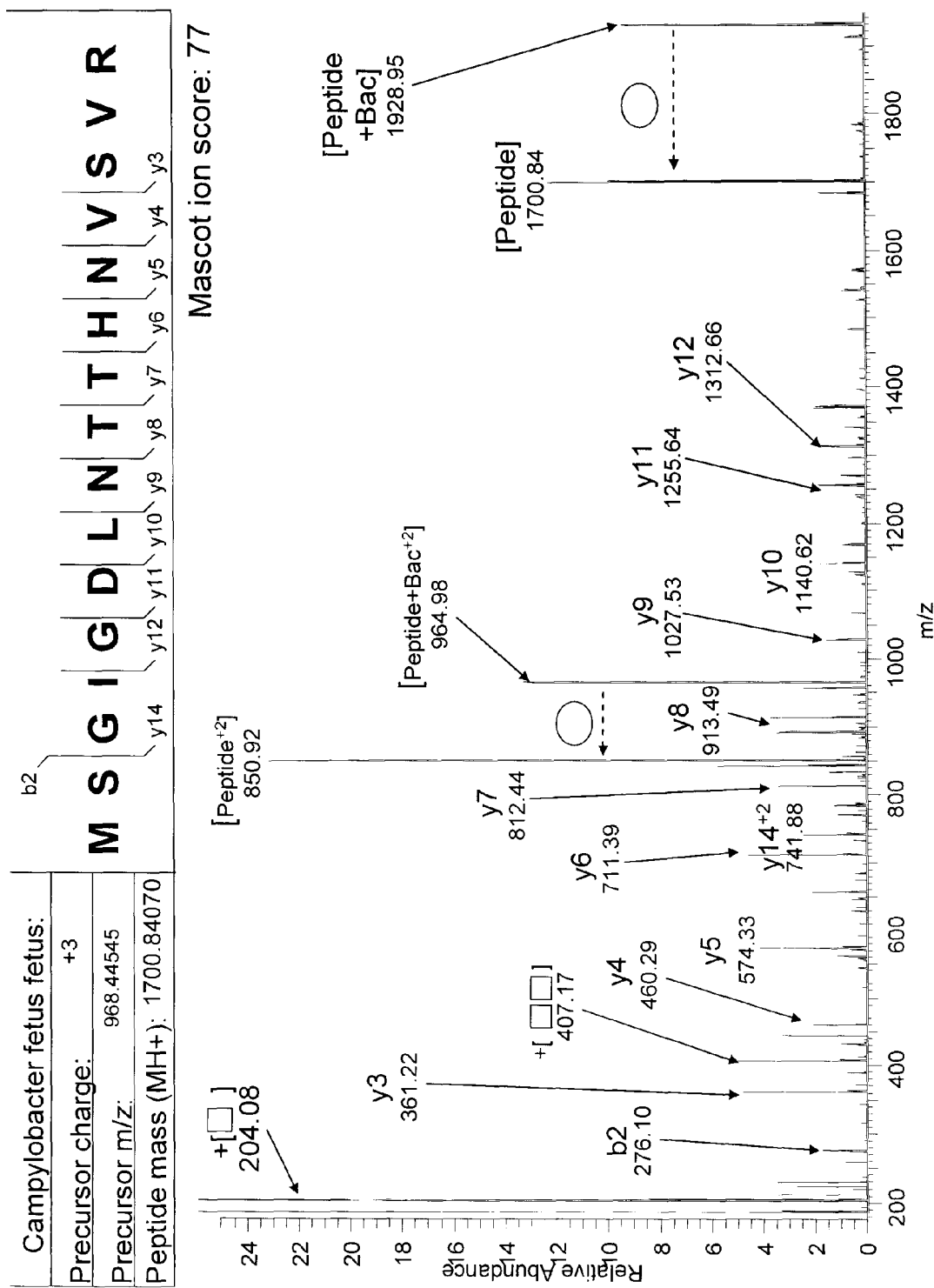

FIG. 8 shows an immuno-blot with antiserum that was raised against the single BSA-glycoconjugates: 120 µg of whole cell lysates from either *C. jejuni* 11168 wild-type (lane 1), *C. jejuni* 11168 pglB mutant strain (lane 2) or *C. fetus fetus* (lane 3) were applied to 12.5% SDS-PAGE. After transfer to a PVDF membrane, the immobilized proteins were probed (FIG. 8A) with a 1:2000 dilution of a serum sample obtained from a rabbit that was immunized with BSA-Formula 1B compound (SZR-1) and with (FIG. 8B) serum of a rabbit immunized with BSA-Formula 1A compound (SZR-3). Molecular weight markers (MW in KDa) are indicated on the left.

Example 8

Formula 1A and 1B Compounds are N-Linked

Cells were grown in MH broth under microaerobic conditions, harvested by centrifugation and washed twice in 50 mM Tris-HCl, pH 7.2. Pellets were freeze dried and placed in 1.5 ml Lobind tubes (Eppendorf). Pellets (10 mg) were resuspended in 1 ml ice-cold Tris-HCl (pH 7.5) in the presence of 150 units of Benozanase, vortexed to resuspend and kept on ice. After sonication (6 times 30 seconds with 1 minute on ice between) the cellular debris was removed by centrifugation at 20,000×g for 30 minutes at 4° C. The supernatant was collected in LoBind (Eppendorf) tubes and freeze dried. Sample processing, glycopeptide enrichment and mass spectrometry were applied as described (Scott N E, et al Molecular and Cellular Proteomics, 2010). Formula 1A and Formula 1B N-linked to asparagines located in polypeptides derived from proteolytic digested cell lysates were identified for *C. fetus fetus*, *C. fetus venerealis* and *C. concisus* (Table 3).

Glycopeptides were isolated and identified from *Campylobacter fetus fetus*, *Campylobacter fetus venerealis*, and *Campylobacter concisus* with the results shown in Table 3. The glycan portions there of all comprised the compound of Formula 1A or 1B.

TABLE 3

Formula 1A and Formula 1B compounds containing glycopeptides

| | Protein name | peptide sequence | Area of HexNAc4-Hex-Bac glycoform (Formula 1B) | Area of HexNAc5-Bac glycoform (Formula 1A) | Ratio (HexNAc5-Bac (Formula 1A)/HexNAc4-Hex-Bac (Formula 1B) |
|---|---|---|---|---|---|
| Identified_glycopeptides_from_Campylobacter_fetus fetus | | | | | |
| Accession number (uniprot) | | | | | |
| A0RM44_CAMFF | PDZ domain protein | 109NSTEMGHIK118 | 9915111 | 25419948 | 2.563758288 |
| A0RN17_CAMFF | Putative cytochrome c family protein | 47YAKDENVSINVYK59 | 8804978 | 25437438 | 2.888983709 |
| A0RN17_CAMFF | Putative cytochrome c family protein | 50DENVSINVYK59 | 1509926 | 7656723 | 5.070925992 |
| A0RM98_CAMFF | Cytochrome c oxidase accessory protein CcoG | 374VHEYYFDVNDTR386 | 19342158 | 5383759 | 0.278343244 |
| A0RP44_CAMFF | Copper homeostasis protein CutF | 85SDDNETFYFK94 | 373909 | 1910579 | 5.10974328 |
| A0RRM2_CAMFF | Mechano-sensitive ion channel family protein | 47NASLGHDLDSLK58 | 4565871 | 14763004 | 3.233337955 |
| A0RP42_CAMFF | Hydroxylamine oxidase | 283MSGIGDLNTTHNVSVR299 | 14116580 | 44662532 | 3.16383515 |
| A0RM84_CAMFF | Soluble lytic murein transglycosylase | 155FLNDNNITSSFIPHLSSNWQFK177 | 310080 | 638344 | 2.058642931 |
| A0RN61_CAMFF | Putative uncharacterized protein | 68FGLGDDNNETTK79 | 3488453 | 20563891 | 5.894845366 |
| Identified_glycopeptides_of_Campylobacter_fetus venerealis | | | | | |
| Accession number (GenBank) | | | | | |
| ACLG01000782.1; C. fetus venerealis Azul-94 Contig782 | PDZ domain protein | 109NSTEMGHIK118 | 2200609 | 1611018 | 0.732078257 |
| unknown | unknown | DTNQTFTK | 4891730 | 7235352 | 1.479098806 |
| unknown | unknown | NFHDTNK | 4045072 | 2602866 | 0.643465926 |
| Identified glycopeptides of *Campylobacter concisus* | | | | | |
| unknown | unknown | (NF)HDTNK | 4261136 | 16308843 | 3.827346276 |

List of proteins identified to be N-linked with Formula 1A and Formula 1B. The single peak areas for Formula 1A and Formula 1B were determined by multiple reaction monitoring (MRM) mass spectrometry.

FIGS. 9A-F depict MS spectra showing that both Formula 1A and Formula 1B compounds are N-linked (to the same peptide), as follows:

9A) MS spectrum (precursor ion scan) of tryptic digested, HILIC-LC enriched peptides; (B) Quantification of relative peak areas of the corresponding ions; (C) MS/MS of the carbohydrate portion, (D) MS/MS of the peptide portion of the m/z ion 968.44545; 9E) MS/MS of the carbohydrate portion, and 9F) MS/MS of the peptide portion of the m/z ion 982.12069.

Example 9

Formula 1A and 16 are Presented on the *Campylobacter* Cell Surface

Cells of *C. fetus fetus, C. fetus venerealis, C. concisus, C. hyointestinais*, and *C. jejuni* were grown on MH plates for 18-24 hours under microaerobic conditions. Cells were harvested from the plate with 2 ml MH broth, cooled on ice for 10 min, centrifuged for 5 min at 6,000×g. Cells were kept on ice for all further labeling and washing steps using pre-cooled (4° C.) solutions. Cells were washed twice with 2 ml washing buffer (50 mM potassium phosphate, 100 mM NaCl). To prevent unspecific binding cells were blocked with 1% Skim Milk in washing buffer for 30 min. Primary antibody (1:1,000 dilution in washing buffer with 0.5% Skim) was applied for 30 min. Cells were washed 3 times with 2 ml Washing buffer. Fluorescent labeled secondary antibody (anti-Rabbit-IgG-Alexa-Flour546, diluted 1:100 in washing buffer with 0.5% Skim Milk) was applied for 30 min and cells were washed 4-times in washing buffer. Cell surface labeling was monitored using a Leica DMRXA Upright Microscope equipped with an Optronics MacroFire Digital Camera (LM-MFCCD). Each picture was taken under identical software settings. *C. jejuni* that produces Structure 1 served as a negative control.

Figure 10:
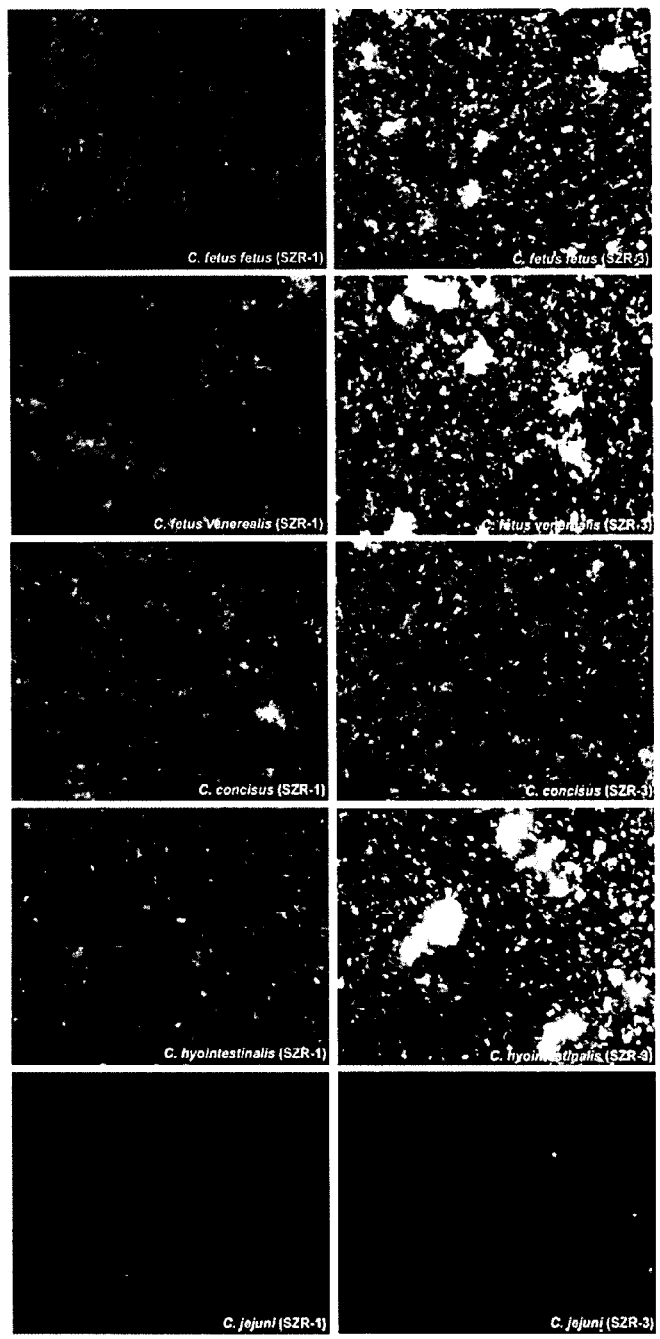
FIG. 10 depicts *campylobacter* cells that were labeled with Formula 1A and Formula 1B-specific antiserum.

FIG. 10 shows fluorescent microscopy images of whole cells of *C. fetus fetus, C. fetus venerealis, C. concisus, C. hyointestinalis*, and *C. jejuni* (negative control) probed with 10A, SZR-1 (anti-Formula 1B) or 106, SZR-3 (anti-Formula 1A) as the primary antiserum and a fluorescent-tagged secondary antibody.

Figure 11:
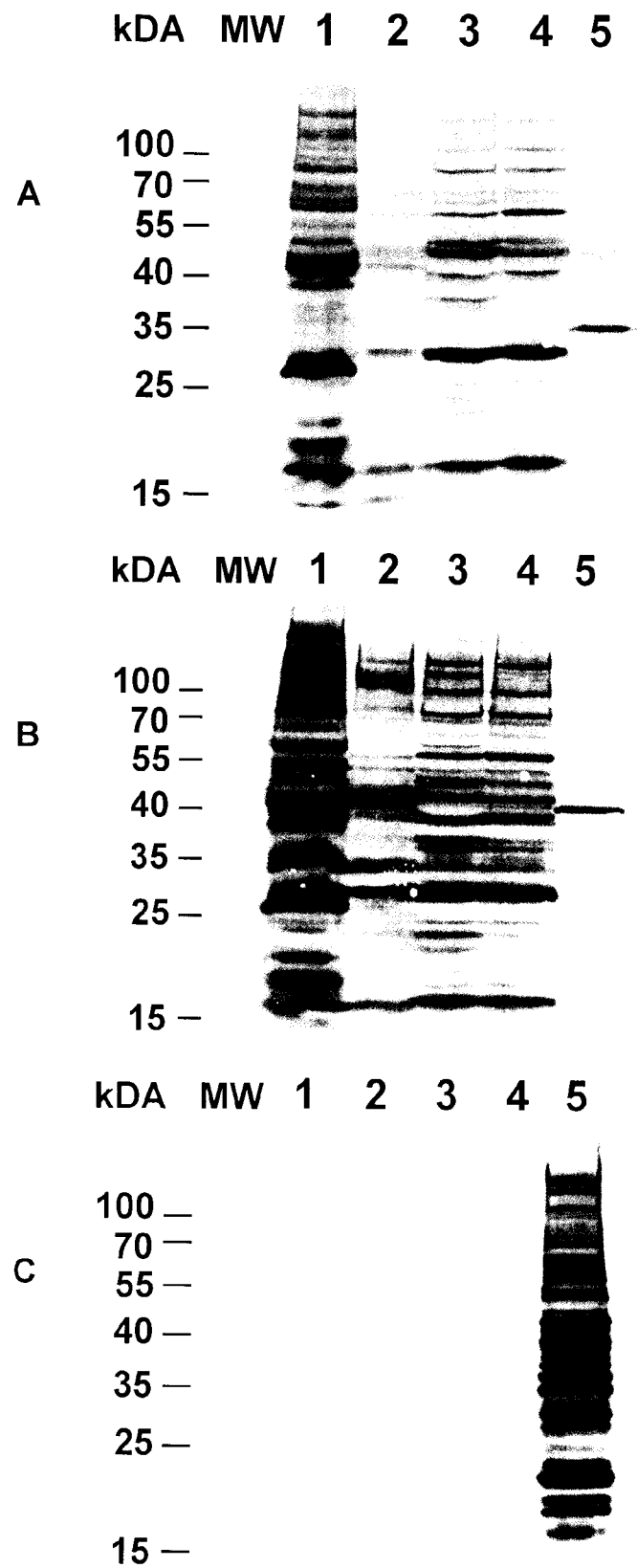
FIG. 11 illustrates immunoblots with antiserum raised Formula 1A, Formula 1B and structure 1.

FIG. 11 shows immunoblots with antiserum that was raised either against Formula 1A or Formula 1B or with an antiserum that targets the N-glycan of *C. jejuni* (structure 1, hR6 was described by Schwarz et al., Nature Chemical Biology, 2010). 90 µg of *C. fetus fetus* (lane 1), *C. fetus venerealis* (lane 2), *C. concisus* (lane 3), *C. hyointestinalis* (lane 4) and *C. jejuni* 11168 (lane 5) were applied to 12.5% SDS-PAGE. After transfer to a PVDF membrane the immobilized proteins were probed with (A) a 1:500 dilution of a serum sample obtained from a rabbit that was immunized with BSA-Formula 1B compound (SZR-1), with (B) a 1:500 dilution serum of a rabbit immunized with BSA-Formula 1A compound (SZR-3) or (C) with a 1:5,000 of an antiserum specific against the N-glycan of *C. jejuni* (hR6). Molecular weight markers (MW in KDa) are indicated on the left.

The glycan compounds (Formula 1A and Formula 1B) can be attached to various glycan carriers (peptides, lipids). The resulting compounds can be used to stimulate an immune-response against the respective structure that will be protective against infection with Formula 1A and Formula 1B presenting bacterial species.

Generated antisera/antibodies can be used (when i.e immobilized on a surface) as a diagnostic to detect e.g. *C. fetus venerealis* or *C. fetus fetus* in infected livestock (especially *C. fetus venerealis* cattle) or to detect human pathogenic *Campylobacter* strains (e.g *C. concisus, C. hyointestinalis, C. ureolyticus*). Said antisera/antibodies can be used to detect compounds in any body fluid or secretion. For example, bull semen could be tested with antibodies recognizing the glycan of Formula 1 to detect *Campylobacter fetus venerealis* infection that may be present in the animal.

The compounds of the present invention can be used to immunize animals, in particular livestock, against *C. fetus venerealis, C. fetus fetus*, and other *Campylobacter* species in which the glycan described herein is native to the organism. Immunization can take the form of treating or preventing disease in individual animals or on a herd-wide basis for improved productivity and health of the herd.

To the extent that *Campylobacter* species in which the glycan of Formula 1 is native to the organism, the compounds described herein can be used in a similar fashion to the above for preparing vaccines to treat or prevent infection by such organisms within humans. As well, a similar diagnostic function can be obtained in humans, using the antibodies or antisera raised against such compounds. Similarly, the compounds can be targeted by other therapeutics such as bacteriophages or their receptor binding proteins.

The present invention has been described by way of various embodiments thereof. It will be understood by persons skilled in the art that the invention is not limited in scope to such embodiments. Rather, the full scope of the invention encompasses and may be appreciated by reference to this patent specification in its entirety, including the claims thereof, and including modifications, variations, and alternative embodiments that would be understood to the skilled person based on said specification.

We claim:

1. An isolated or purified compound comprising A-GlcNAc[GlcNAc]-GalNAc-GalNAc-QuiNAc4NAc, wherein A is GlcNAc or Glc and wherein said compound is free from *Campylobacter* sp. cell wall components.

2. An isolated or purified compound comprising A-GlcNAc[GlcNAc]-GalNAc-GalNAc-QuiNAc4NAc connected or linked to a single amino acid, an oligopeptide, a peptide, a protein, or a lipid, wherein A is GlcNAc or Glc and wherein said compound is substantially free from *Campylobacter* sp. cell wall components.

3. The compound of claim 2 wherein said single amino acid is asparagine.

4. An immunogenic composition comprising the compound of claim 1.

5. The immunogenic composition of claim 4, further comprising an adjuvant.

6. A method of treating or reducing an infection caused by a *Campylobacter* organism, comprising administering the immunogenic composition of claim 4 to an animal or human in need thereof, wherein the compound comprises a glycan that is native to said organism.

7. The method of claim 6 wherein said organism is *Campylobacter fetus venerealis, Campylobacter fetus fetus, Campylobacter concisus, Campylobacter hyointestinalis, Campylobacter hyointestinalis* subspecies, *Campylobacter sputorum, Campylobacter sputorum* subspecies, *Campylobacter lanienae, Campylobacter ureolyticus, Campylobacter hominis, Campylobacter gracilis, Campylobacter rectus, Campylobacter showae, Campylobacter mucosalis*, or *Campylobacter curvus*.

* * * * *